(12) United States Patent
Schoelling

(10) Patent No.: US 7,833,210 B2
(45) Date of Patent: Nov. 16, 2010

(54) TAMPON FOR FEMININE HYGIENE AND PROCESS AND APPARATUS FOR MANUFACTURING THE SAME

(75) Inventor: Hans-Werner Schoelling, Ennepetal (DE)

(73) Assignee: Johnson & Johnson GmbH, Neuss (DE)

( * ) Notice: Subject to any disclaimer, the term of this patent is extended or adjusted under 35 U.S.C. 154(b) by 988 days.

(21) Appl. No.: 10/586,019

(22) PCT Filed: Sep. 26, 2003

(86) PCT No.: PCT/EP03/10721

§ 371 (c)(1),
(2), (4) Date: Jan. 3, 2007

(87) PCT Pub. No.: WO2004/028428

PCT Pub. Date: Apr. 8, 2004

(65) Prior Publication Data

US 2007/0083182 A1     Apr. 12, 2007

(30) Foreign Application Priority Data

Sep. 26, 2002   (DE)   ................................. 102 44 874

(51) Int. Cl.
*A61F 13/20* (2006.01)
(52) U.S. Cl. ............................ 604/385.17; 604/385.18; 604/11; 604/904; 604/12
(58) Field of Classification Search ............. 604/11–18, 604/904, 385.17, 385.18
See application file for complete search history.

(56) References Cited

U.S. PATENT DOCUMENTS

| | | | |
|---|---|---|---|
| 2,798,260 | A | 7/1957 | Niepmann et al. |
| 3,422,496 | A | 1/1969 | Wolff et al. |
| 4,816,100 | A | 3/1989 | Friese |
| 4,859,273 | A | 8/1989 | Friese |
| 4,863,450 | A | 9/1989 | Friese |
| 5,047,024 | A | 9/1991 | Glassman |
| 5,458,835 | A | 10/1995 | Wilkes et al. |
| 5,592,725 | A | 1/1997 | Brinker |
| 5,832,576 | A | 11/1998 | Leutwyler et al. |
| 5,911,712 | A * | 6/1999 | Leutwyler et al. ........... 604/379 |
| 6,283,952 | B1 | 9/2001 | Child et al. |
| 6,310,269 | B1 | 10/2001 | Friese et al. |
| 6,433,246 | B1 * | 8/2002 | Nguyen et al. .............. 604/375 |

(Continued)

FOREIGN PATENT DOCUMENTS

DE             944419 C       6/1956

(Continued)

*Primary Examiner*—Jacqueline F. Stephens

(57) ABSTRACT

The invention relates to a tampon for feminine hygiene, with a tapered introductory end, a withdrawal end provided with a withdrawal means and a longitudinal axis, comprising a longitudinally extending absorbent body made from compressed fiber material, the absorbent body being densified more intensely in the region of the longitudinal axis and forming a fiber column, from which longitudinal ribs extend radially outward and flank longitudinal ribs in pairs. The tapered introductory end being formed by the to fiber column, the longitudinal grooves and longitudinal ribs is provided with collecting grooves and collecting ribs to collect menstrual secretions, wherein the collecting grooves are open axially to the front and radially outward and wherein the collecting ribs flank the collecting grooves in pairs. The invention provides for an increased absorption capacity of the tampon in relation to the weight of the fiber material per tampon.

25 Claims, 16 Drawing Sheets

U.S. PATENT DOCUMENTS

| | | | |
|---|---|---|---|
| 6,939,340 B1 * | 9/2005 | Berges | 604/385.17 |
| 2001/0011169 A1 | 8/2001 | Taylor et al. | |

FOREIGN PATENT DOCUMENTS

| | | |
|---|---|---|
| DE | 3347649 C | 8/1988 |
| EP | 301874 A | 2/1989 |
| EP | 403636 B | 10/1994 |
| WO | WO 00/53141 A | 9/2000 |
| WO | WO 02/078586 A | 10/2002 |

* cited by examiner

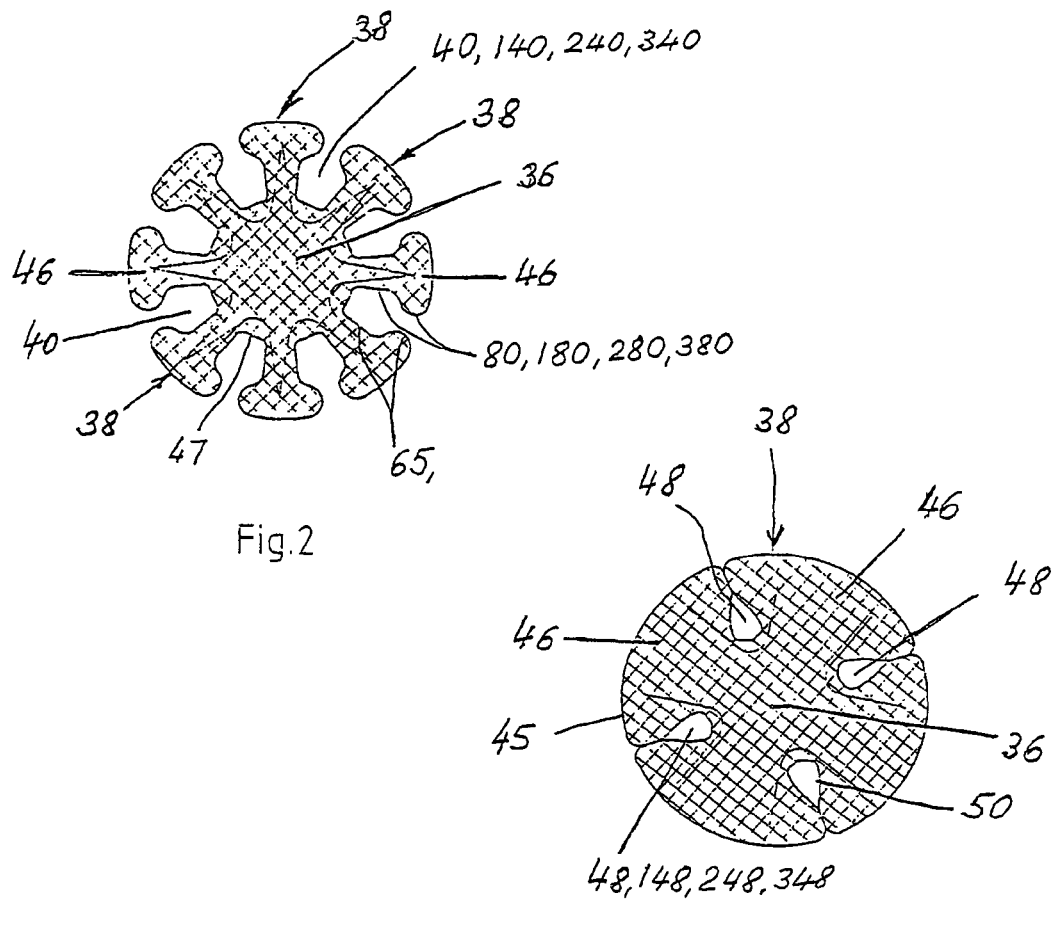
Fig.2
Fig.3
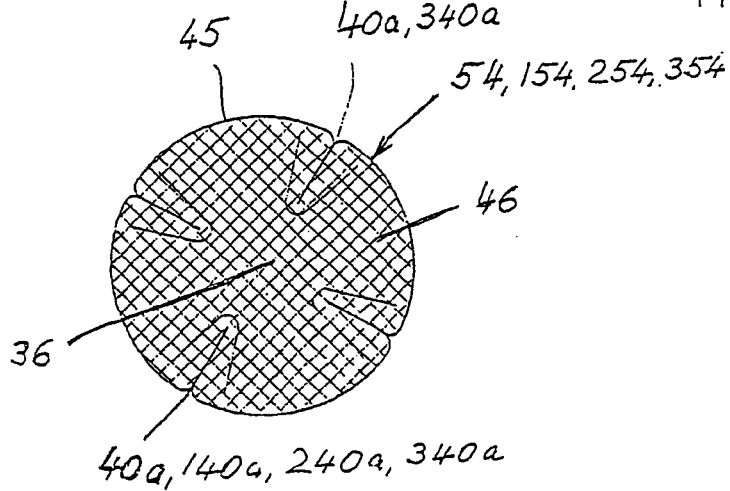
Fig.4

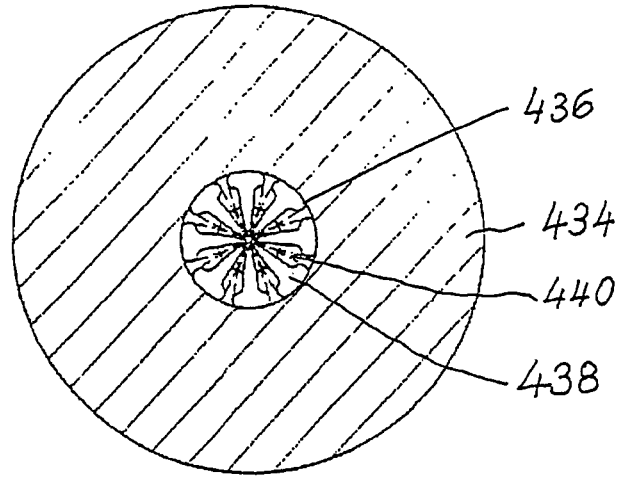
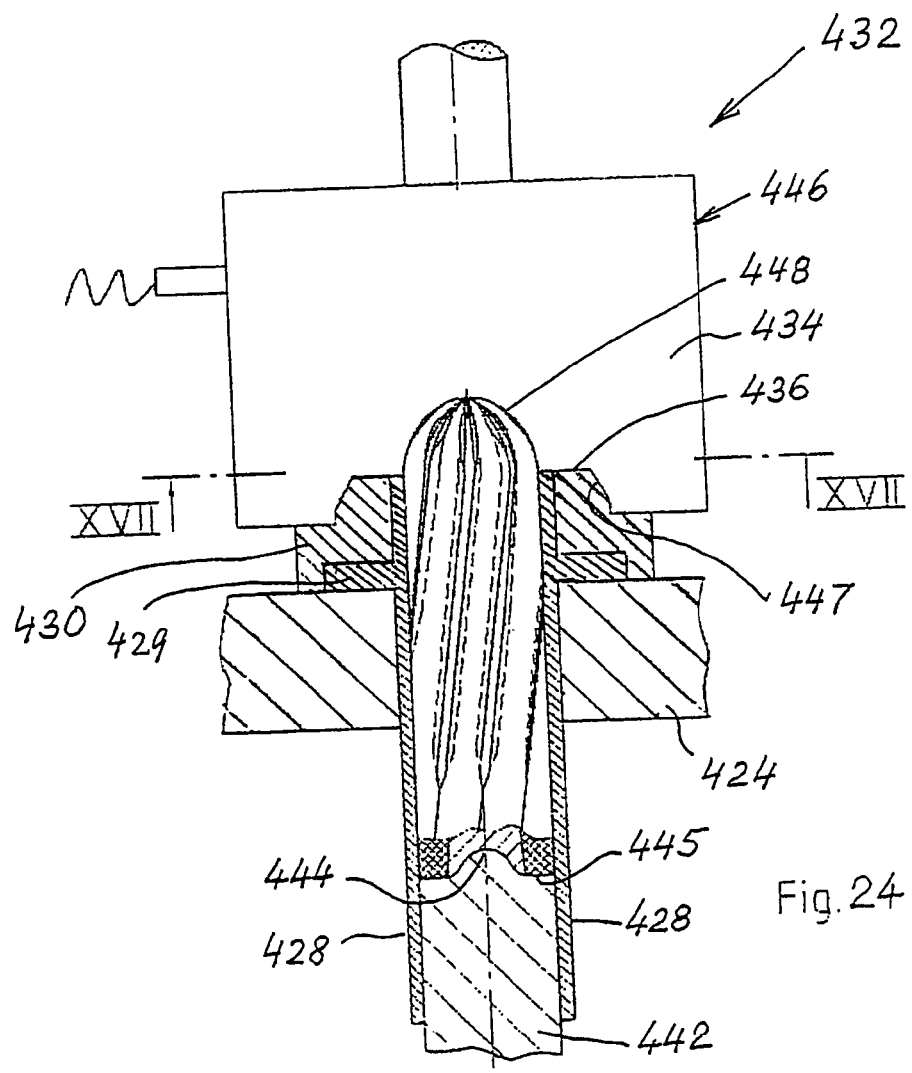
Fig. 25
Fig. 24

TAMPON FOR FEMININE HYGIENE AND PROCESS AND APPARATUS FOR MANUFACTURING THE SAME

This application is the national phase filing under 371 of international application PCT/EP2003/010721 filed on Sep. 26, 2003.

The invention relates to a tampon for feminine hygiene and to a process and an apparatus for manufacturing a tampon according to the independent claims 1, 26 and 48.

A tampon of the aforementioned generic type and processes and apparatuses for manufacturing the same are described in U.S. Pat. No. 6,310,269 (Friese et al.) and U.S. Pat. No. 5,832,576 (Leutwyler et al.). Tampons with pressed grooves are known from U.S. Pat. No. 2,798,260 (Niepmann et al.) and U.S. Pat. No. 3,422,496 (Wolff et al.). Tampons of the aforementioned generic type are also known from DE 944 419, FIG. 7, DE 33 47 649 C2, FIG. 6 and EP 0 403 636 B1, FIG. 19.

The fiber material of these tampons is densified more intensely in the region of a fiber column, in order to achieve a high rigidity of the tampon. This rigidity is necessary in particular in the event that the tampon is used as a digital tampon. The inwardly open grooves of such tampons have the advantage of increasing the circumferential surface area of the tampon, with which menstrual secretions are intended to come into contact and be absorbed. However, there are certain limits to the absorption of such menstrual secretions. This is because the tapered introductory end has a substantially closed, complex, hemispherical or conical to paraboloidal form, the outer surface of which consists of fiber material which is axially pressed more intensely. The reason for this is that, after it has been ejected from the press, the introductory end of the tampon has a front face which is directed perpendicular to the longitudinal axis of the tampon and is formed by a respective end of the longitudinal ribs and longitudinal grooves and of a central fiber column of more intensely pressed fiber material. Since the mold for tapering the introductory end of the tampon has a concave recess, the form of which corresponds to the tapering of the introductory end, the fiber material at the ends of the longitudinal ribs in particular is not only pressed and widened axially in the direction of the recovery end of the tampon but also in the circumferential direction of the tampon when the mold is pressed against the introductory end of the tampon. As a consequence of this, the longitudinal grooves at the introductory end are closed by the pressed fiber material of the longitudinal ribs. This has the effect of hindering the immediate take-up and absorption of menstrual secretions by the tampon and their rapid conduction into the longitudinal grooves of the tampon and consequently to the more intensely pressed fiber material of the fiber column, the utilization of which is extremely desirable for an improved absorption capacity of such a tampon. Furthermore, in the case of the aforementioned known tampons, menstrual secretions, in particular of a liquid consistency, can flow unhindered through the longitudinal grooves, which are open toward the circumferential surface of the tampon, up to and out of the withdrawal end before the menstrual secretions are absorbed to the desired extent by the fiber material of the tampon. The fact that, as mentioned, the fiber material in the fiber column is pressed more intensely to ensure the rigidity of the tampon also contributes to this effect, with the result that the immediate absorption of the menstrual secretions takes place predominantly by the less densified fiber material in the longitudinal ribs. That is to say that a significant part of the fiber material can only be used inadequately for the absorption of menstrual secretions.

The invention is therefore based on the object of improving a tampon of the generic type stated at the beginning in such a way that the absorption capacity of the tampon, relative to the weight of the fiber material used per tampon, can be increased.

The invention achieves this object by the tapered introductory end, which is formed by the fiber column, the longitudinal grooves and longitudinal ribs, being provided with collecting grooves and collecting ribs to collect menstrual secretions, wherein the collecting grooves are open axially to the front and radially outward and wherein preferably the collecting ribs flank the collecting grooves in pairs.

This has the effect of creating an enlarged surface area of the introductory end of the tampon which is structured by the collecting ribs and collecting grooves and by which the menstrual secretions can be absorbed more rapidly and also by the fiber material at the introductory end of the tampon. In addition, menstrual secretions not absorbed by the introductory end can be conducted directly into the longitudinal grooves and into the longitudinal ribs flanking them on the circumferential surface of the tampon, because, according to a further feature of the invention, the collecting grooves go over continuously into the longitudinal grooves and the collecting ribs go over continuously into the longitudinal ribs at the end of the tapered introductory end.

This effect can be further improved by the collecting grooves having a substantially trough-shaped cross section and the collecting ribs having a narrow cross section which is tapered outward, and in addition a middle longitudinal portion of the collecting grooves having a greater width than the longitudinal grooves. Since the collecting ribs are more intensely densified than the longitudinal ribs, an increased rigidity of the tampon at the introductory end is achieved, which is desired for a digital tampon.

To achieve quicker and better utilization of the absorption capability of the tampon also in the region of the circumferential surface of the tampon, it is recommendable according to a further feature of the invention to form the tampon in such a way that the longitudinal grooves are slightly undercut in the transverse profile and form radial collecting pockets (280), the longitudinal ribs having a slightly T-shaped transverse profile. In this case, the longitudinal grooves and longitudinal ribs may have this cross section or the mentioned transverse profile over the entire length of the tampon.

According to a particularly preferred embodiment of the tampon according to the invention, however, it Is recommended that the longitudinal grooves have a slightly undercut transverse profile of a collecting pocket from the rear end of the tapered introductory end, wherein said undercut transverse profile is increasingly drop-shaped toward the withdrawal end, wherein the longitudinal grooves are gradually narrower at the circumferential surface of the tampon and are closed in the region of a security zone at the withdrawal end to form collecting channels for menstrual secretions. It is advantageous furthermore that the drop-shaped transverse profile of the longitudinal grooves is radially widened toward the fiber column. As a consequence of this, body fluid can be absorbed to a greater extent by the fiber material of the fiber column. In this case, the fiber column is expediently pressed approximately cylindrically along its entire length, in order to ensure the rigidity or cross-breaking resistance of the tampon during the insertion into the body cavity.

According to an embodiment of the invention, the longitudinal grooves, longitudinal ribs and collecting channels may extend approximately parallel to the tampon axis. Depending on the physiological conditions, a tampon of this more simple construction satisfies the requirements for menstruation protection to be met by a tampon.

If there are higher requirements for the absorbency of a tampon, a tampon in which the longitudinal grooves, longitudinal ribs and collecting channels extend spirally or helically around the longitudinal axis of the tampon is particularly advantageous, it being possible for the circumferential angle to be up to 190°. As a result, the absorbent surface area of the tampon is markedly increased, while moreover the advantageous structure of the tampon is retained. Therefore, the absorption capacity of the tampon can be increased in relation to the fiber material used per tampon.

According to a further embodiment of the tampon according to the invention, some of the longitudinal grooves may end in the region of a security zone which is provided at least in the region of the withdrawal end of the tampon. This configuration of the tampon requires less intensive pressing of the fiber material, at least at the withdrawal end, with the result that the desired spreading out of the fiber material at the withdrawal end is facilitated and the tampon feels more pleasant. For this purpose, the longitudinal ribs may be radially pressed less intensively in the region of the security zone. Furthermore, the security zone performs the task of counteracting leakage in the event of an increased amount of menstrual secretions being issued, because the fiber material is distributed and pressed more uniformly over the cross section of this security zone. This has the effect of ensuring a more uniform capillary action, which is conducive to the absorption of menstrual secretions.

In addition, the fiber structure of the tampon can be varied by the fiber material of the longitudinal ribs being radially pressed increasingly less intensively from the introductory end up to the region of the withdrawal end and therefore being softer at the circumferential surface of the tampon than at the introductory end. Technical manufacturing-related advantages, which are discussed in more detail below, are also obtained as a result.

Furthermore, the arrangement of the security zone in the region of the withdrawal end of a tampon is advantageous if the fiber material of the security zone is hydrophobically impregnated. This allows menstrual, in particular fluid, secretions which come into contact with the security zone to be stopped by the hydrophobic fiber material of the security zone and forced back in the direction of the absorbing fiber material and prevented from leaking out. The axial length of the security zone is expediently 5 to 15 mm.

Furthermore, a finger recess may be axially pressed into the withdrawal end of the tampon, wherein at least the more intensely densified fiber material of the finger recess forms the axial closure at the end of the collecting channels extending up to the withdrawal end. The axial length of the more intensely densified fiber material of the finger recess is expediently up to approximately 5 mm.

Furthermore, the outer surface of the tampon may be at least partially surrounded by a fluid-permeable cover, which may consist of a nonwoven layer or a perforated foil and is preferably hydrophobic. Such a cover smooths the outer surface of the tampon and thereby facilitates its insertion into the body cavity and at the same time prevents the detachment of fibers during insertion into the body cavity and removal from the same.

The invention also relates to a process for manufacturing a tampon for feminine hygiene, comprising steps as follows:

a) providing a tampon blank comprising a longitudinally extending absorbent body of random fiber material, the length of the tampon blank corresponding approximately to the length of the tampon, b) pressing the tampon blank to form a preform (406) of a round cross section with a more intensely densified fiber column in the region of the longitudinal axis of the preform (406) and forming substantially longitudinally extending grooves and ribs alternating in the circumferential direction at an outer circumferential surface of the preform (406), and c) tapering the introductory end of the preform (406), wherein, to complete the tampon, the fiber column, the longitudinal grooves and longitudinal ribs are formed during their tapering into collecting grooves and collecting ribs at a front end of the preform (406), wherein the collecting grooves are open axially to the front and radially outward.

A particularly advantageous further development of this process consists in that, in step b), at least some of the longitudinal grooves and longitudinal ribs are pressed along the entire length of the tampon blank, such that the transverse profile of the longitudinal grooves is slightly undercut and the transverse profile of the longitudinal ribs is formed into a slight T-shape, wherein the longitudinal ribs are radially pressed less intensively at least in the region of the withdrawal end of the tampon associated with the outlet end of the press, so that the tampon blank has a greater diameter at least on this longitudinal portion and that, thereafter, the radially outer ends of at least these longitudinal ribs are radially compressed by exerting a slight concentric pressure, such that the tampon blank is reduced to a final diameter of the preform (406), wherein the width of outer ends of the longitudinal ribs positioned at the circumferential surface of the preform (406) and similar to a T-beam are enlarged and thereby the width of the transverse profile of the undercut longitudinal grooves is reduced at the circumferential surface of the preform (406), so that the transverse profile of the longitudinal grooves forms a collecting pocket, and that the longitudinal grooves, of which at least the rear portion associated with the withdrawal end is pressed less intensively, are closed by said concentric pressure to a reduced diameter of the preform to form collecting channels and a security zone having parallel axes within the preform, and that the fiber material within said security zone is densified largely uniformly over the cross section of the preform, such that the collecting channels are increasingly closed axially within this security zone.

Finally, the invention also relates to an apparatus for manufacturing a tampon, having a device for feeding an absorbent body as a tampon blank consisting of random fiber material, the length of the tampon blank corresponding approximately to the length of the tampon, to a press having an inlet side and outlet side and pressing jaws of identical dimensions, which are positioned in a star-shaped arrangement relative to a central press axis and which are radially movable synchronously in a common plane relative to the press axis between their open position and closed position and which support each other at their opposite longitudinal sides in their closed position;

a stepped pressing surface at each of said pressing jaws, wherein the pressing surfaces (458) of the pressing jaws (450) form a press opening of round cross section; and each of said pressing surfaces is provided with a pressing knife which is directed toward the pressing opening and a pressing shoulder which is positioned only at a determined side of the pressing knife and directed in the same circumferential direction around the press axis, the pressing shoulder is outwardly offset with respect to a pressing edge at the free, inner end of the pressing knife relative to the press axis, a surface formed by the pressing shoulder is greater than a surface formed by the pressing edge of the pressing knife, an ejecting device is provided with an ejecting rod, which is coaxially movable to and fro toward the pressing opening, a stepwise movable transportation device is fitted with cylindrical transportation sleeves, which are secured at identical distances on the transportation device, wherein said transportation sleeves, which are open at both ends and have a diameter corresponding approximately to that of a preform that is ejected from the press, can in each case be positioned at the outlet side of the press coaxially to the press axis to receive a preform, a final forming station with a dome former which is axially movable to and fro, the front face of which is provided with a concavely tapered depression, in front of which one of the two open ends of a respective transportation sleeve which is fitted with a preform can be positioned stepwise and coaxially for tapering the introductory end of the preform, and with a recess former which is movable coaxially to the dome former through the other of the two ends of the transport sleeve against the withdrawal end of the preform. According to the invention, it is preferably provided here that pressing ribs and pressing grooves are arranged in an alternating manner in the circumferential direction on the wall of the concavely tapered depression in the dome former, such that the introductory end of the preform, during tapering, can be provided with collecting grooves which are open axially and radially outward and collecting ribs which project axially and radially outward.

The invention is explained in more detail below on the basis of the schematic drawing of several exemplary embodiments, in which:

FIG. 2 shows a cross section of the tampon according to sectional line II-II in FIGS. 1, 5, 8, 9 and 10 with eight longitudinal grooves and longitudinal ribs;

FIG. 3 shows a cross section of the tampon in FIGS. 1, 9 and 10 according to sectional line III-III with four longitudinal grooves which are closed on the outside and form collecting channels in a security zone;

FIG. 4 shows a cross section of the tampon in FIGS. 1, 9 and 10 according to the sectional line IV-IV with axially closed collecting channels in the region of the security zone of the tampon;

FIG. 24 shows a central longitudinal section of a final forming station for the introductory end and the withdrawal end of a preform in a working position, in a horizontal longitudinal section; and FIG. 25 shows a dome former in the form of a die in a cross-sectional view according to sectional line XXV-XXV in FIG. 24.

Figure 1:
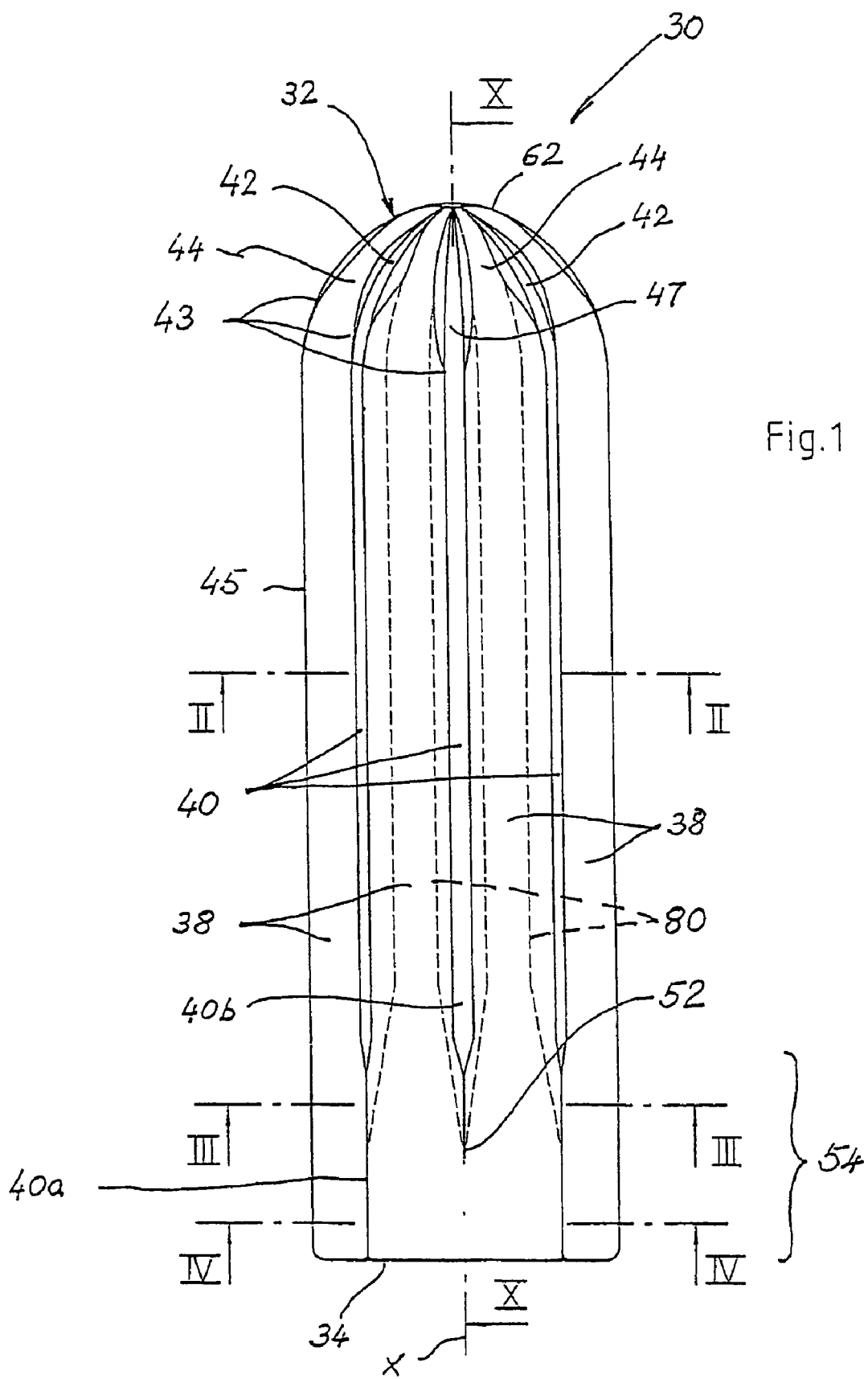
FIG. 1 shows a first embodiment of a tampon according to the invention in a side view, with eight axially parallel longitudinal grooves of the same cross section and also with collecting grooves and collecting ribs at the introductory end.

According to FIGS. 1 to 4, a tampon 30 for feminine hygiene with a tapered introductory end 32, a withdrawal end 34 and a longitudinal axis x is represented. The tampon 30 comprises a longitudinally extending absorbent body made from pressed fiber material. According to FIGS. 2 to 4, a fiber column 36 of more intensely densified fiber material is provided in the region of the longitudinal axis x of the tampon 30, from which column longitudinal ribs 38 extend radially outward and bound longitudinal grooves 40 in pairs.

Figure 10:
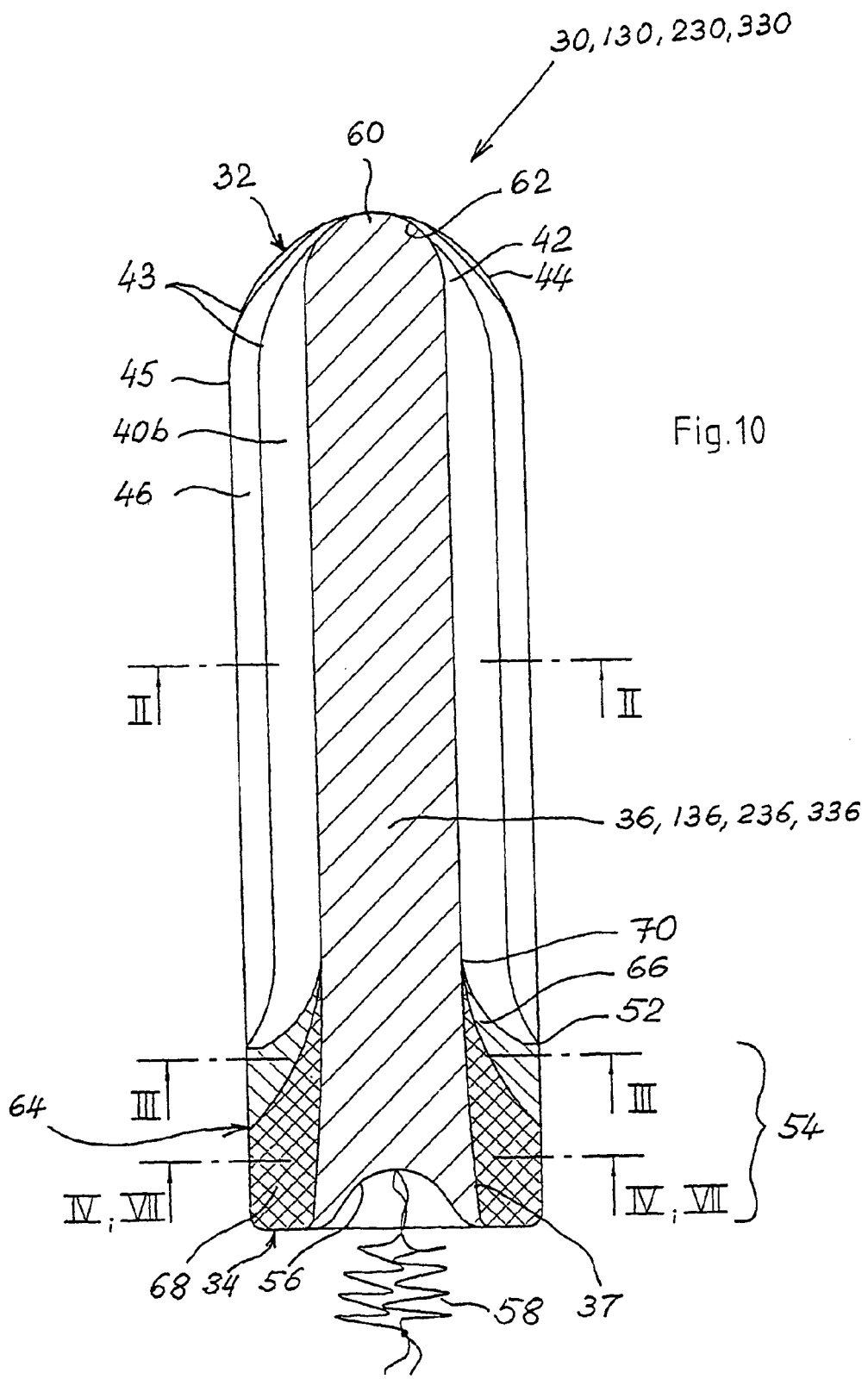
FIG. 10 shows a longitudinal section of the tampon in FIGS. 1, 5, 8 and 9 according to a sectional line X-X.

According to FIGS. 1 and 10, at the introductory end 32 of the tampon 30, the fiber column 36 is tapered and provided with collecting grooves 42 which are V-shaped in transverse profile, are open axially to the front and radially outward and are flanked by collecting ribs 44, which have an inverted V-shaped transverse profile. The V-shaped transverse profile of the collecting grooves 42 in the fiber column 36 continues thereafter in a cross section which is widened in a trough-shaped manner, the width of which is at the greatest midway along the collecting grooves 42 and after that goes over continuously in a transitional region 43 between the tapered introductory end 32 and an approximately cylindrical circumferential surface 45 into a slightly undercut transverse profile of the longitudinal grooves 40, which forms collecting pockets 80 radially toward the fiber column 36 (FIG. 2). In this way it is ensured that a greatest possible amount of menstrual secretions can be collected by the collecting grooves 42 and lead to the longitudinal grooves 40 of the tampon 30, unless the secretions have already been absorbed at the introductory end 32 by the fiber material of the fiber column 36 and by the collecting ribs 44 surrounding the fiber column 36. Since the fiber column 36 is also provided with collecting grooves 42 at the introductory end 32 of the tampon 30, the absorption surface area for body fluids available at the introductory end 32 of the tampon 30 is increased and, at the same time, the fiber material contained in the fiber column 36 is used for the absorption of the menstrual secretions. Since each longitudinal groove 40 forms the axially extended collecting pocket 80, the menstrual secretions which have penetrated into these collecting pockets 80 are partially retained in the collecting pockets 80 as a result of the undercut transverse profile widened in the form of a pocket toward the fiber column 36 and are absorbed by the fiber material surrounding the collecting pockets 80.

The fiber material of the collecting ribs 44 is densified more intensely than the longitudinal ribs 38 behind the introductory end 32. As a result, a greater rigidity is achieved in the region of the introductory end 32, which is desired for the case of digital introduction of the tampon 30 into the body cavity.

According to FIGS. 1 and 2, the longitudinal grooves 40 are open at the approximately cylindrical circumferential surface 45 of the tampon 30 and have an approximately identical transverse profile over their entire length, from the end of the tapered introductory end 32 at the transitional region 43 to their end at a distance before the withdrawal end 34 of the tampon 30 up to the withdrawal end of the same, which profile is shown in FIG. 2.

It can be seen from the cross-sectional representation in FIG. 2 that the longitudinal grooves 40 are slightly undercut and form in transverse profile the collecting pockets 80, because the transverse profile of the longitudinal ribs 38 is slightly T-shaped. The reduced width of the longitudinal grooves 40 in the region of the circumferential surface 45 of the tampon 30, reduced by bars 46 of the longitudinal ribs 38 that are T-shaped in transverse profile, contributes to the partial retention of body fluid conducted from the introductory end 32 into the longitudinal grooves 40 in the cross-sectionally pocket-shaped longitudinal grooves 40, in favor of absorption by the fiber material in the region of the fiber column 36.

FIG. 1 shows that, at a distance before the withdrawal end 34 of the tampon 30, at the circumferential surface 45 of the latter, all the longitudinal grooves 40 are axially closed at 40*a* and form collecting channels 48, as can be seen from the cross-sectional representation in FIG. 3. The collecting channels 48 have a drop-shaped transverse profile 50 and are closed in the region of the withdrawal end 34 (FIG. 4). In this case, the longitudinal grooves 40*a* are closed in the region of the circumferential surface 45 of the tampon 30 by thickened bars 46 of the longitudinal ribs 38 that are T-shaped in transverse profile being substantially wider in comparison with their profile in FIG. 2, so that the ends of the T-bars 46 of neighboring longitudinal ribs 38 on their opposite sides lie against one another and form the substantially soft, closed circumferential surface 45 of the tampon 30. It is evident that the free, approximately drop-shaped transverse profile 50 of the collecting channels 48 widens from the circumferential surface 45 of the tampon 30 in the direction of the fiber column 36, so that a larger wetting surface area for body fluids to be absorbed is available in the region of the more intensely pressed fiber material of the fiber column 36.

FIG. 1 also shows that shorter longitudinal grooves 40*b* provided between the continuous longitudinal grooves 40, 40*a* already end at a distance before the withdrawal end 34 at 52 and are axially closed by the densified fiber material which is located between the ends 52 of these shorter longitudinal grooves 40*b* and the withdrawal end 34, as can be seen in FIGS. 4 and 10. This longitudinal portion of the tampon 30 extending between the ends 52 of the shorter longitudinal grooves 40*b* and the withdrawal end 34 forms a security zone 54 against leakage, wherein the collecting channels 48 in the security zone, which are closed at the circumferential surface 45 of the tampon 30 and increasingly closed toward the withdrawal end 34, prolong the dwell time of the body fluid contained therein and permit absorption of the fluid by the fiber material surrounding the collecting channels 48, in particular in the region of the fiber column 36.

The withdrawal end 34 of the tampon 30 in FIG. 1 is provided according to FIG. 10 with a finger recess 56, which is produced by an axial pressing operation and leads to a more intense densification of the fiber material.

As FIG. 10 shows, this densification has an effect both radially and axially and leads, in the axial direction, to a conically reducing densification profile 64 of the fiber material. The finger recess 56 serves for the application of a finger for introducing the tampon 30 into the body cavity and makes it possible to spread out the fiber material at the withdrawal end 34 for less penetrative introduction of the tampon 30, whereby at the same time the immediate absorbency of the fiber material in this region is improved.

Since, according to FIG. 10, the fiber material is pressed more intensely in the region of this finger recess 56 over the entire cross section of the tampon 30 than over the remaining longitudinal region of the tampon 30, the collecting channels 48 shown in FIG. 3 are, as can be seen from FIG. 4, completely closed not only radially but also axially in this region by the pressed fiber material. The finger recess 56 therefore constitutes part of the security zone 54, because the more intensely densified fiber material of the finger recess 56 closes the collecting channels 48 toward the withdrawal end 34 and improves absorption of the body fluid contained therein by the fiber material of the security zone 54 surrounding the collecting channels 48.

The fibers which are used for manufacturing the absorbent body preferably contain regenerated cellulose fibers, natural fibers and/or synthetic fibers. Particularly preferred are hydrophilic fibers, which absorb fluid. Apart from natural fibers, worked fibers, such as regenerated cellulose, cellulose nitrate, cellulose acetate, rayon, polyester, polyvinyl alcohol, polyolefin, polyamine, polyamide, polyacrylonitrile and the like are also suitable. Furthermore, fibers of different cross section, in particular with a multiply branched cross section, can be used, as are obtainable for example under the trade name DanufilRVY as multiply branched viscose rayon fibers from Acordis UK Ltd, Sponson, England. These fibers are described in U.S. Pat. No. 5,458,835 (Wilkes et al.) and EP 0 301 874.

Although the entire fiber material used for a tampon may have hydrophilic properties, it is preferred to use, at least partly, for the security zone 54 fiber material which is coated with a hydrophobic material. Such coating material is obtainable for example under the trade name BK 204/FL with the designation Galaxy from the company Henkel AG. In many cases, a fiber blend of 70% by weight hydrophobic fibers and 30% by weight hydrophilic fibers proves to be particularly suitable. The predominantly or entirely hydrophobic finish of the fiber material used for the security zone 54 makes it possible to counteract leakage and to deflect body fluid which has reached the security zone 54 for absorption into the region of hydrophilic fibers of the tampon, in particular to the fiber column 36.

According to FIG. 10, a withdrawal cord 58 extends from the withdrawal end 34 of the tampon 30 and serves for removing the tampon 30 from the body cavity. The withdrawal cord 58 preferably consists of a hydrophobic cotton material, which prevents the withdrawal cord 58 from absorbing body fluid.

Represented in FIG. 10 is a longitudinal section corresponding to the sectional line X-X of the tampon 30 in FIG. 1, which is also valid for the embodiments described further below of the tampon according to the invention if spiral longitudinal ribs and longitudinal grooves of these tampons are imagined as having been transferred into the plane of the drawing. For the sake of simplicity, only the reference numerals of FIG. 1 are used; however, under the aforementioned condition, they may also be respectively preceded by a digit of one, two or three for the embodiments described further below of a tampon 130, 230 and 330 according to the invention.

As can be seen, FIG. 10 shows the tampon 30 on which some of the longitudinal grooves, that is the longitudinal grooves 40*b*, end before the security zone 54. Accordingly, the tampon 30 comprises the coaxial fiber column 36, the fiber material of which is more intensely densified by the radial pressing of the longitudinal grooves 40, 40*b*. A front end 60 of the fiber column 36, lying at the introductory end 32 of the tampon 30, is tapered and contains in the region of this tapering 62 of the fiber column 36 the collecting grooves 42, which are V-shaped in transverse profile, after that widen in a trough-shaped manner and then go over into the pocket-shaped transverse profile of the longitudinal grooves 40, so that their bases 47 have a width which corresponds to that of the then adjoining longitudinal grooves 40 in the region of the approximately cylindrical circumferential surface 45 of the tampon 30. The collecting grooves 42 and longitudinal grooves 40 consequently enclose the fiber column 36 of the tampon 30, which has a substantially cylindrical form.

In FIGS. 2 and 10, the longitudinal grooves 40 extend to the left and right from the fiber column 36, are narrower in the region of the circumferential surface 45 of the tampon 30 as a result of the horizontal bars 46 of a T-shaped transverse profile 65 of the longitudinal ribs 38 defining the circumferential surface 45, and are therefore effective in the radially inner region for collecting menstrual secretions, both in the cross section in the form of the collecting pockets 80 and in the longitudinal direction in the form of the gradually closing collecting channels 48 toward the withdrawal end 34 of the tampon 30.

Furthermore, in FIG. 10, the cross section III-III referring to FIG. 3 reveals that the security zone 54 has at the end of the longitudinal grooves 40*b* a densification zone 66 of the fiber material which is directed conically toward the fiber column 36 and toward the introductory end 32 and in which the fiber material is densified to a lesser extent than a densification zone 68 which extends up to the withdrawal end 34, extends through the front, less densified zone 66 in the direction of the introductory end 32 up to approximately the front end 70 of the latter and, behind the front densification zone 66, radially and axially forms the withdrawal end 34 of the tampon 30. The axial impressing of the finger recess 56 into the rear end of the fiber column 36 at the withdrawal end 34 has had the effect that, in the region of the finger recess 56, the fiber material of the fiber column 36 has been displaced not only axially but also radially, with the result that the fiber column 36 has a longitudinal portion 37 widening conically toward the finger recess 56 and, in the region of the widening of the fiber column 36 from the Withdrawal end 34 in the direction of the introductory end 32 of the security zone 54, the conically reducing densification zones 66, 68 are present.

Figure 5:
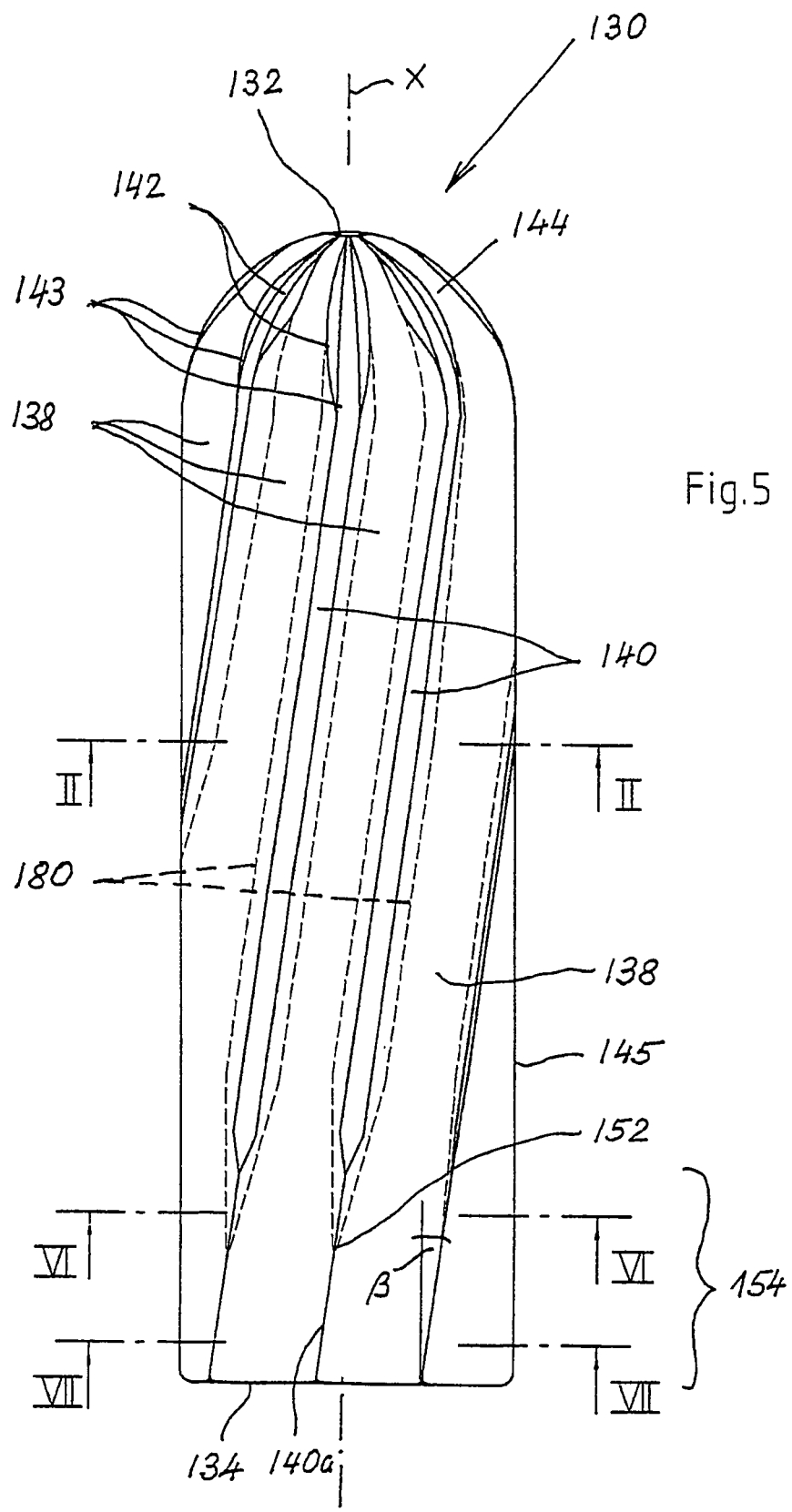
FIG. 5 shows a second embodiment of a tampon in a side view, with eight spiral longitudinal ribs and longitudinal grooves of the same cross section.

FIG. 5 shows a second embodiment of a tampon according to the invention, the reference numerals of the tampon 30 in FIGS. 1 to 4 and 10 being preceded by a digit 1 for the same or similar features. The tampon 130 is consequently a variant of the tampon 30 in FIG. 1. In the case of this tampon 130, provided around a fiber column 136 are longitudinal grooves 140, which extend spirally or helically over the circumferential surface 145 of the tampon 130. These longitudinal grooves 140 form with a generatrix of the tampon 130 an acute angle of lead β up to about 30°, the circumferential angle α, over which the longitudinal grooves 140 extend over a cylindrical circumferential surface 145 of the tampon 130, being between 120° and 190° (not represented). As a result, the circumferential surface 145 of the tampon 130 is enlarged and the dwell time of menstrual secretions in the spiral longitudinal grooves 140 is prolonged. Here, too, the longitudinal grooves 140 are flanked by longitudinal ribs 138, which extend longitudinally, parallel to the longitudinal grooves 140, spirally or helically over the circumferential surface 145 of the tampon 130.

As in the case of the tampon 30 in FIGS. 1 to 4 and 10, the introductory end 132 of the tampon 130 in FIG. 5 is provided with initially V-shaped and then trough-shaped collecting grooves 142 of large cross section and with collecting ribs 144 which in cross section taper outward in an inverted V-shaped manner. As FIG. 5 shows, the collecting grooves 142 and collecting ribs 144 extend radially with respect to the longitudinal axis x of the tampon 130 and, in a region 143, go over continuously into the spiral form of the longitudinal grooves 140, forming collecting pockets 180 which are slightly undercut in transverse profile (FIG. 2), or into the longitudinal ribs 138, which are slightly T-shaped in transverse profile. As in FIG. 1, the tampon 130 is provided with eight collecting grooves 142 and eight longitudinal grooves 140 which, however, as FIG. 5 shows, run helically or spirally, in order to utilize better the absorption capacity of the fiber material by the enlarged surface area. The longitudinal grooves 140 of the tampon 130 have in FIG. 5 a pocket-shaped transverse profile, which corresponds substantially to that of the tampon 30 in FIGS. 1 to 4. However, the tampon 130 differs from the tampon 30 in FIG. 1 to the extent that all the longitudinal ribs 138 and longitudinal grooves 140 extend up to the withdrawal end 134 of the tampon 130. However, it is the case with the embodiment in FIG. 5, too, that the longitudinal grooves 140 are open radially outward only up to a beginning 152 of a security zone 154 and are once again closed at the circumferential surface 145 of the security zone 154 by laterally touching bars 146 of the T-shaped longitudinal ribs 138, in order to form eight collecting channels 148, as the sectional representation in FIG. 6 reveals.

Figure 6:
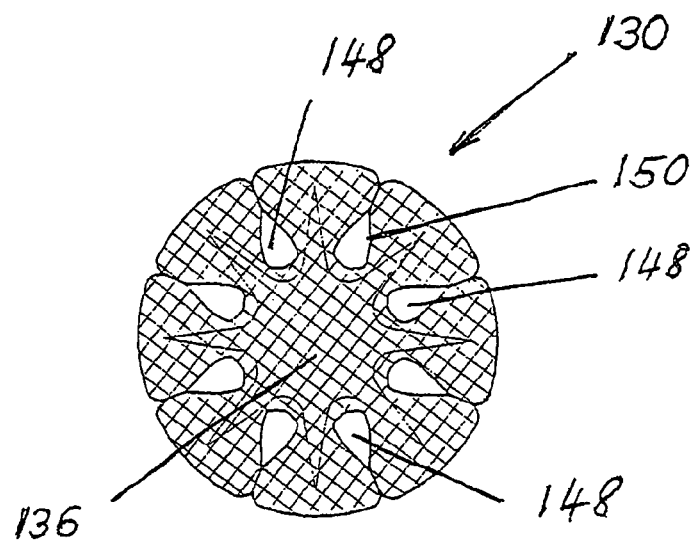
FIG. 6 shows a cross section of the tampon in FIGS. 5, 8 and 10 according to sectional line VI-VI with eight collecting channels, which are closed at the circumferential surface of the tampon and are axially closed, in a security zone.
Figure 7:
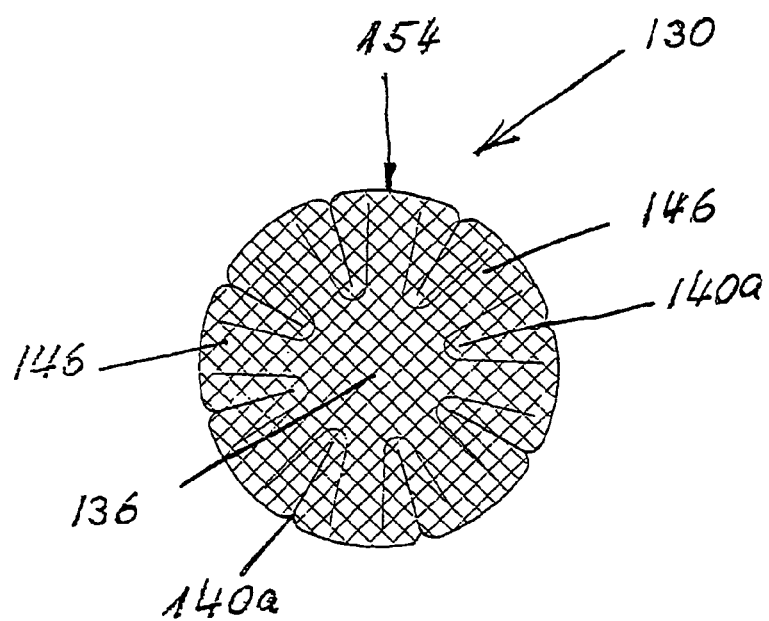
FIG. 7 shows a cross section of the tampon in FIGS. 5, 8 and 10 according to sectional line VII-VII with eight collecting channels which are closed in the region of a withdrawal end.

Accordingly, along with the spiral pressing of the eight longitudinal grooves 140, the difference from the tampon 30 in FIG. 1 is that, as FIG. 6 shows, all eight longitudinal grooves 140 extend as collecting channels 148 into the security zone 154 with an approximately drop-shaped transverse profile 150, but, as in the case of the tampon 30 in FIG. 1, are closed both axially and radially in the region of the cross section at 140*a* according to FIG. 7, which is associated with the security zone 154 or the finger recess 56 in FIG. 10, because in this region the bars 146 of the T-shaped longitudinal ribs 138 are greatly widened by radial pressing, such that their opposite side faces lie closely against one another and therefore close the collecting channels 148.

Figure 8:
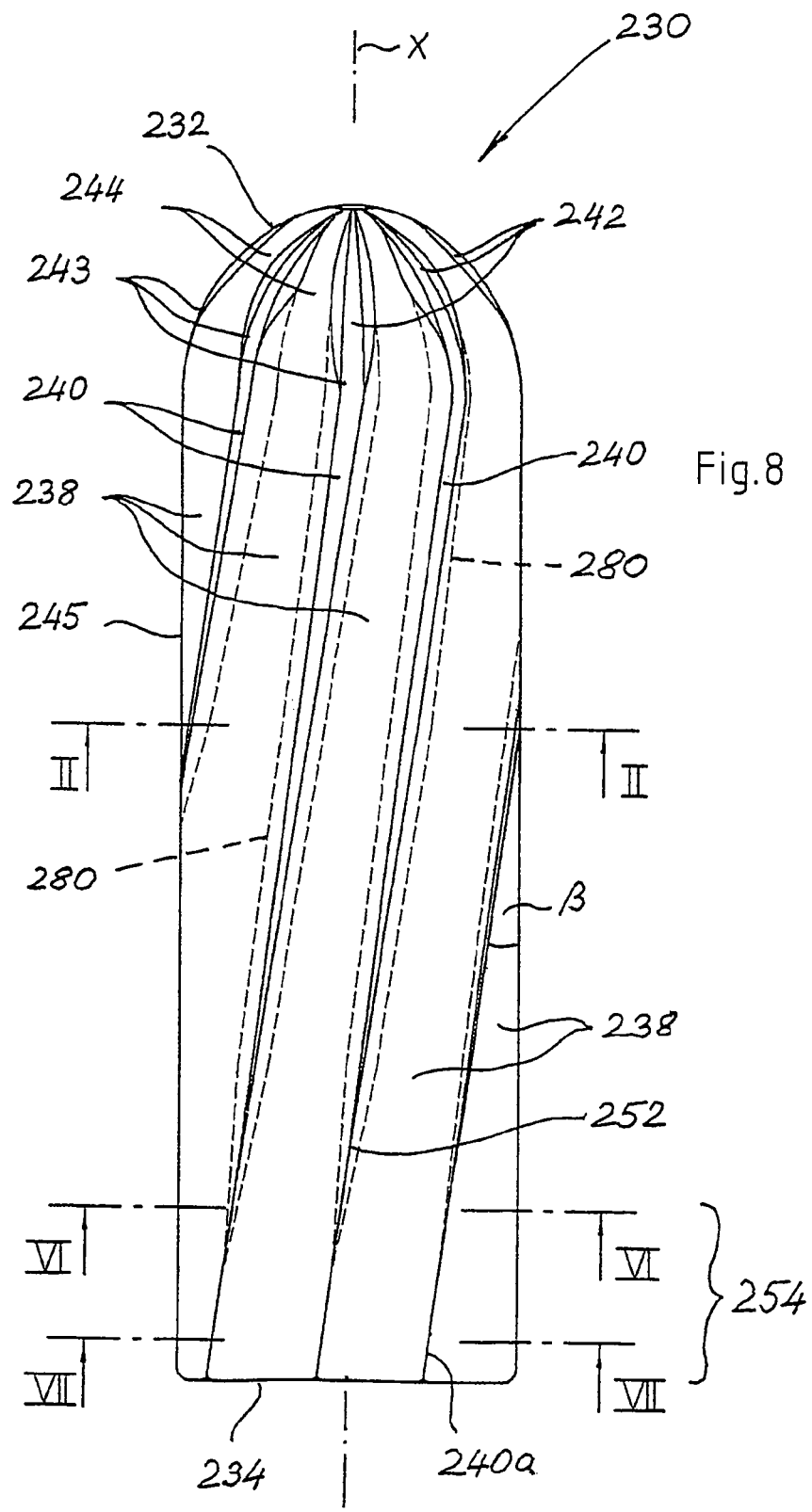
FIG. 8 shows a third embodiment of a tampon in a side view, with eight spiral longitudinal grooves and longitudinal ribs, which are increasingly closed outwardly and axially, forming collecting channels in the region of a security zone.

A particularly advantageous third embodiment of the tampon 230 according to the invention is shown in FIG. 8. While an introductory end 232 of the tampon 230 is likewise provided with eight collecting grooves 242 and collecting ribs 244 which are radial with respect to the longitudinal axis x and correspond to those of the two tampons 30, 130 in FIGS. 1 and 5, the initially once again V-shaped and then very trough-shaped collecting grooves 242 are continuously adjoined in a transitional region 243 between the introductory end 232 and an approximately cylindrical circumferential surface 245 by spirally or helically running, slightly undercut longitudinal grooves 240 and longitudinal ribs 238, which form collecting pockets 280 in transverse profile and have a slightly T-shaped transverse profile 265 (FIG. 2).

This tampon 230 is distinguished by the fact that the collecting-pocket-shaped transverse profile of the longitudinal grooves 240 (FIG. 2) is increasingly smaller in the region of the circumferential surface 245 of the tampon 230 after the transitional region 243 in the direction of a withdrawal end 234 and goes over ever increasingly into a drop-shaped transverse profile 250 of smaller cross section (FIG. 6), as described on the basis of FIG. 2, and increasingly closes on itself both radially outward at 240a and in the axial direction toward the withdrawal end 234, thereby forming collecting channels 248, as FIG. 7 shows.

This radial and axial closure of the collecting channels 248 formed by the longitudinal grooves 240 before the withdrawal end 234 of the tampon 230 comprises the pressed fiber material of a security zone 254 or the finger recess 56 in the same. The reduction in the width and cross section of the longitudinal grooves 240 in the direction of the withdrawal end 234 is consequently achieved by the T-shaped transverse profile 256 of the longitudinal ribs 238 becoming increasingly compressed radially toward a fiber column 236 and increasingly wider in the circumferential direction of the tampon 230.

In this case, a bar 246, which becomes increasingly wider toward the withdrawal end 234 (FIGS. 6 and 7), of this T-shaped transverse profile 265 of the longitudinal ribs 238 defines the circumferential surface 245 of the tampon 230. These bars 246 of the T-shaped longitudinal ribs 238 become ever increasingly closer at their ends lying in the circumferential direction to the opposing ends of the bars 246 of neighboring longitudinal ribs 238, until they lie against one another and close the longitudinal grooves 240 on the outer side of the tampon 230, thereby forming the collecting channels 248 at the circumferential surface 245, as is shown in the cross-sectional representation in FIG. 6. As mentioned with reference to FIG. 8, this cross section lies at the beginning 252 of the security zone 254, which is characterized by the outwardly closed, substantially cylindrical circumferential surface 245 and in which the drop-shaped transverse profile 250 of the longitudinal ribs 240 forms in the direction of the withdrawal end 234 of the tampon 230 the outwardly closed collecting channels 248, which are also axially closed in the region of the security zone 254, as FIG. 7 shows.

Here, too, the withdrawal end 234 of the tampon 230 according to FIG. 10 is provided with the withdrawal cord 58 and the finger recess 56, in the region of which the fiber material, as mentioned, is more intensely densified, with the result that it is also the case with this embodiment of the tampon 230 that the longitudinal grooves 240 are closed at the withdrawal end 234 by the more intensely densified fiber material of the finger recess 56.

It goes without saying that, by means of the collecting pockets 280, which are outwardly open in transverse profile, of the collecting grooves 240 according to FIG. 2, in combination with the collecting channels 248, menstrual secretions are retained within the pocket-shaped longitudinal grooves 240 and collecting channels 248 and, as a result, are absorbed better by the fiber material of a central fiber column 236 of the tampon 230 and, accordingly, the absorbency of the fiber material can be utilized more exhaustively.

Figure 9:
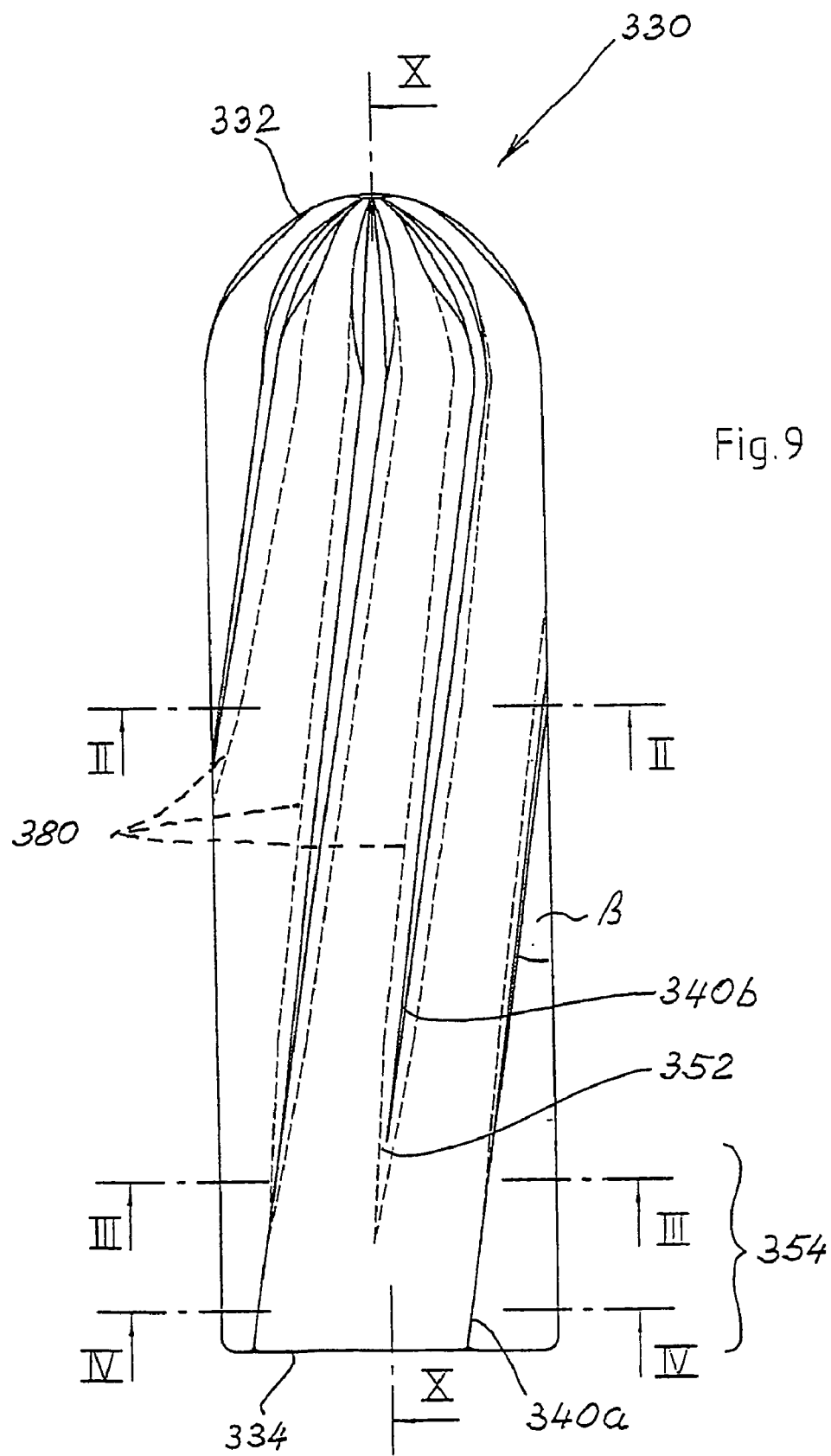
FIG. 9 shows a fourth embodiment of a tampon in a side view, with four longitudinal ribs continuing up to the withdrawal end and four longitudinal grooves which are increasingly closed outwardly and axially, forming collecting channels in the region of a security zone.

FIG. 9 shows a fourth embodiment of the tampon 330 according to the invention, which differs from the tampon 230 in FIG. 8 only to the extent that, as in the case of the tampon 30 in FIG. 1, although longitudinal ribs 338 and longitudinal grooves 340 alternate in the circumferential direction, only some of the longitudinal grooves 340 extend up to a withdrawal end 334 of the tampon 330 and some of the other longitudinal grooves 340a extend only up to the beginning 352 of a security zone 354 provided in the region of the withdrawal end 334 and are also axially closed there. On the other hand, an introductory end 332 of the tampon 330 is identical to the introductory ends 32, 132, 232 of the tampons 30, 130, 230 in FIGS. 1, 5 and 8, so that to this extent you are referred to the above description of these tampons.

As in the case of the previous configurations of the tampons 30, 130 and 230 in FIGS. 1, 5 and 8, the tampon 330 in FIG. 9 is also provided with eight longitudinal grooves 340, whereby only four longitudinal grooves 340b extend up to the withdrawal end 334, as already described on the basis of the tampon 30 shown in FIG. 1 and the cross-sectional representation in FIG. 3. Owing to the more intensely densified fiber material in the security zone 354 and to a finger recess 56 (see FIG. 10) of the tampon 330, said recess terminating the security zone at the withdrawal end 334, the longitudinal grooves 340 extending to the withdrawal end 334 are axially increasingly closed radially outward, in order to form collecting channels 348.

As mentioned, it is recommendable for the fiber material of the security zone 354 to be hydrophobically impregnated in order to prevent leakage. The axial length of the security zone 354 at the withdrawal end 334 should be 5 to 15 mm between the radially outwardly open end 352 of the longitudinal grooves 340 forming collecting pockets 380 and the intensely densified fiber material of the finger recess 56 shown in FIG. 10. In the region of the finger recess 56, it is recommendable to make the axial length of the fiber material that is densified more intensely here up to about 5 mm. It goes without saying that these dimensional specifications can be used for all the tampons 30, 130, 230 and 330 described, but of course can be changed according to the specific intended purpose, size and structure of the tampon concerned.

Although the tampons according to the invention can be manufactured from absorbent bodies of any desired composition of the absorbent material, such as fiber material, absorbent bodies which comprise a longitudinally extending strip of fiber fleece, which is known per se and therefore not shown, are preferred for the manufacture of the tampons according to the invention, said strip of fiber fleece having a determined length and a width corresponding approximately to the length of the tampon and being wound up, upon itself to form a blank and subsequently pressed into the final form of the tampon. The withdrawal cord 58 according to FIG. 10, which is placed around the strip of fiber fleece and knotted before the strip of fiber fleece is wound up upon itself, may serve as the withdrawal means.

Furthermore, when using an absorbent body consisting of fiber material, in particular one with a composition such as that described above, it is recommendable to surround the outer surface of the tampon at least partially with a fluid-permeable cover (not represented), as known per se. This cover may comprise a nonwoven layer and/or a perforated foil. Such a cover is preferably hydrophobic, with the result that fluid can be absorbed through it by the absorption material lying underneath.

An apparatus 400 for manufacturing the particularly preferred tampon 230 in FIG. 8 is described below on the basis of FIGS. 11 to 25.

Figure 11:
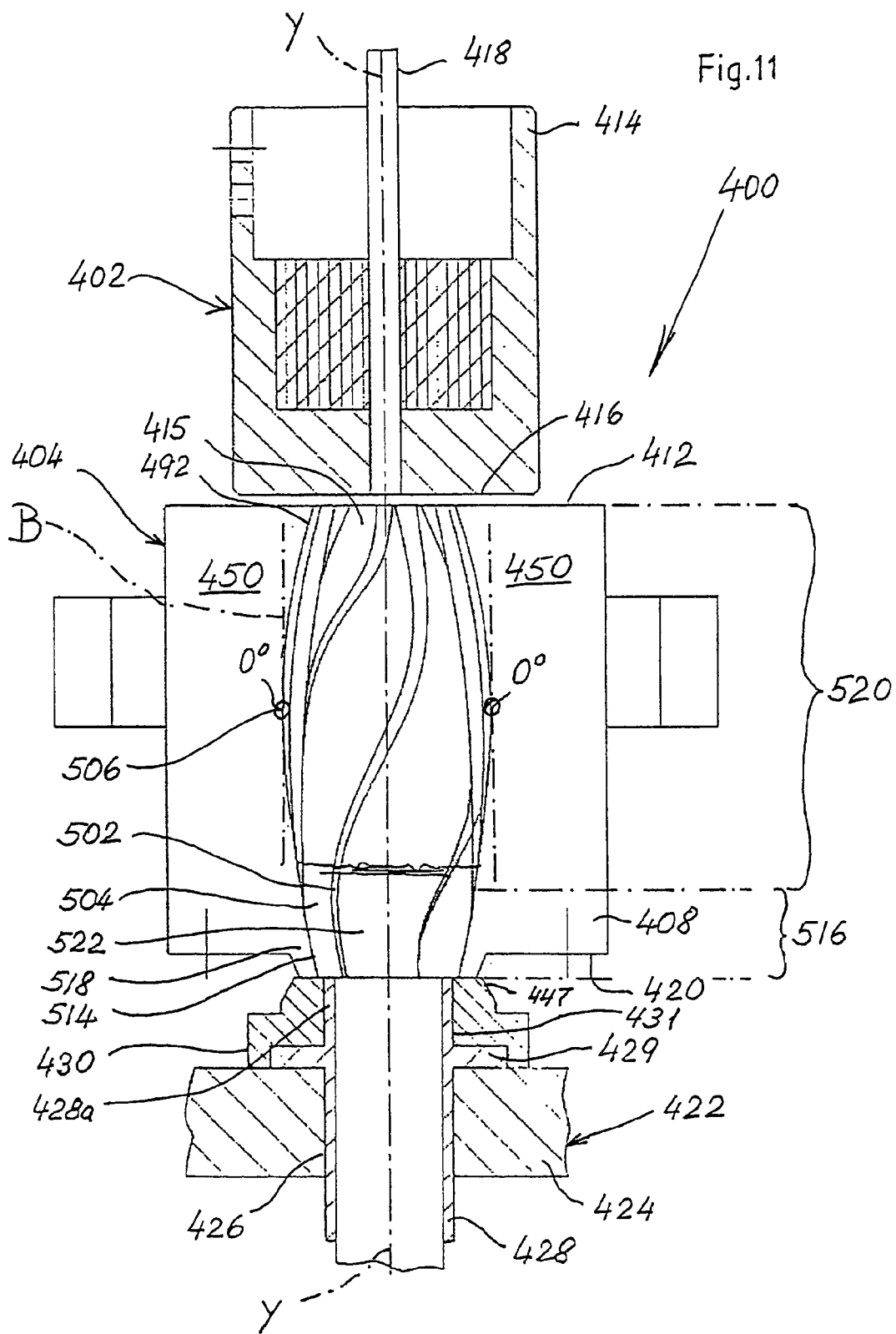
FIG. 11 shows a combined press and diameter reduction device in a central longitudinal section, with a plan view of two opposite pressing jaws in a position between the open position and closed or pressing position.
Figure 20:
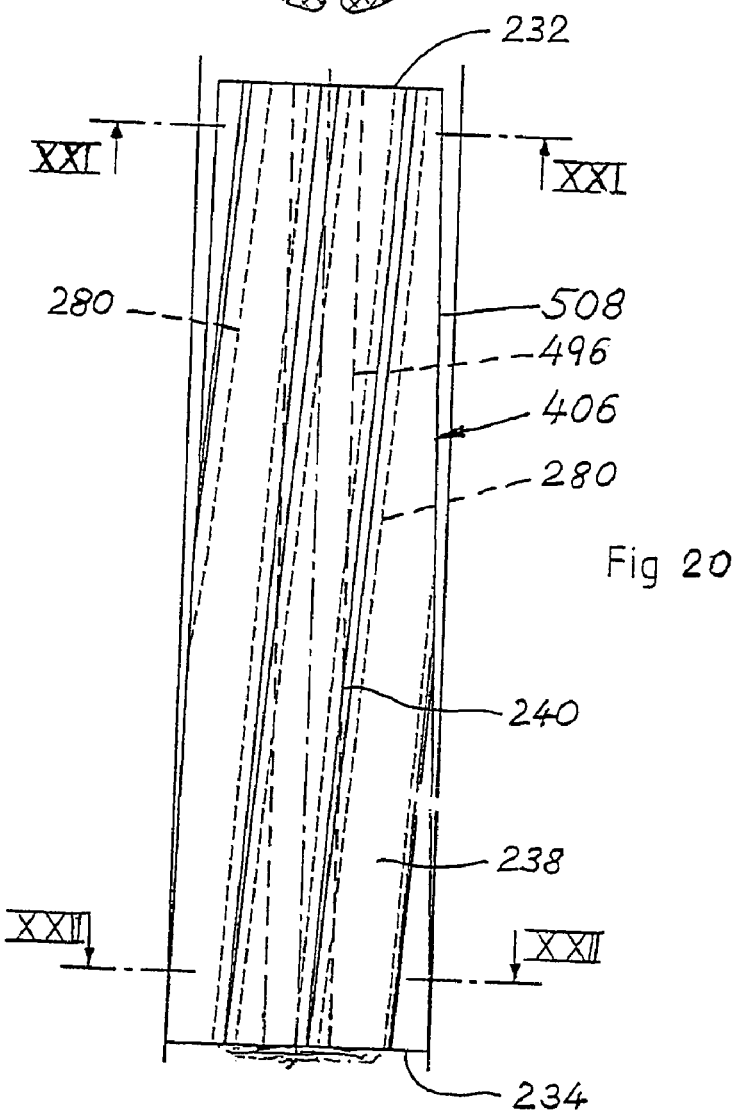
FIG. 20 shows a view of a preform which has been pressed in the press and the circumferential surface of which tapers conically toward the introductory end and the longitudinal grooves of which are increasingly narrower outwardly toward the withdrawal end.
Figure 22:
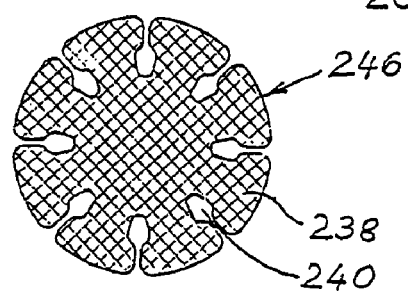
FIG. 22 shows a cross section of the preform according to sectional line XXII-XXII in FIG. 20 in the region of its withdrawal end.

According to FIG. 11, the apparatus 400 is provided with a combined feeding and ejecting device 402 for feeding a tampon blank (not shown) comprising a strip of fiber fleece wound up upon itself to a press 404 for pressing a preform 406, which is represented in FIG. 20, and also for ejecting this preform 406 from the press 404 into a transportation device 422. The preform 406 may already be used as a tampon in conjunction with sleeve-shaped or tubular applicators which are known per se and are therefore not represented.

Furthermore, according to the invention, a diameter reduction device 408 for reducing the diameter of the preform 406 to a final diameter of the finished digital tampon 230 is integrated into the press 404.

In FIGS. 24 and 25, a final forming station 410 for forming the collecting grooves 242 and collecting ribs 244 during the tapering of the introductory end 232 of the preform 406 is arranged downstream of the press 404, with the stepwise circulating or revolving transportation device 422 interposed.

The combined feeding and ejecting device 402 is associated with an inlet side 412 of the press 404, in the case of which a feeding ram 414 has a front face 416 corresponding to the cross section of a press opening 415 in the opened state of the press 404. Within the feeding ram 414, an ejecting rod 418 is mounted coaxially movably to and fro, the diameter of which is adapted to the cross section of the preform 406 in FIG. 20.

Also represented in a broken away form in FIG. 11, at an outlet side 420 of the press 404, is the transportation device 422, which is movable stepwise transversely with respect to the longitudinal axis y of the press 404 and comprises a flexible, endless member for a disk-shaped transportation element 424, which has a plurality of transverse bores 426, into which a transportation sleeve 428 is respectively inserted. Each of these transportation sleeves 428 has a diameter which corresponds approximately to the final closed diameter of the press opening 415 at the outlet side 420 of the press 404. In FIG. 11, the transportation sleeve 428 is shown coaxially behind the press 404 in a receiving position for a preform 406 according to FIG. 20. The transportation sleeve 428 has an annular flange 429, by which it is is fastened to the side of the transportation element 424 facing the press 404 by means of a centering cap 430 by riveting, screwing, welding or the like. The centering cap 430 has a cylindrical bore 431, into which an entry stub 428a of the transportation sleeve 428 is inserted, the end of which terminates flush with the outer side of the centering cap 430. As a result of this, every preform 406 ejected from the press 404 and the diameter reduction device 408 combined with the latter into the transportation sleeve 428 has downstream of the diameter reduction device 408 its final cylindrical form of a specific final diameter.

Figure 12:
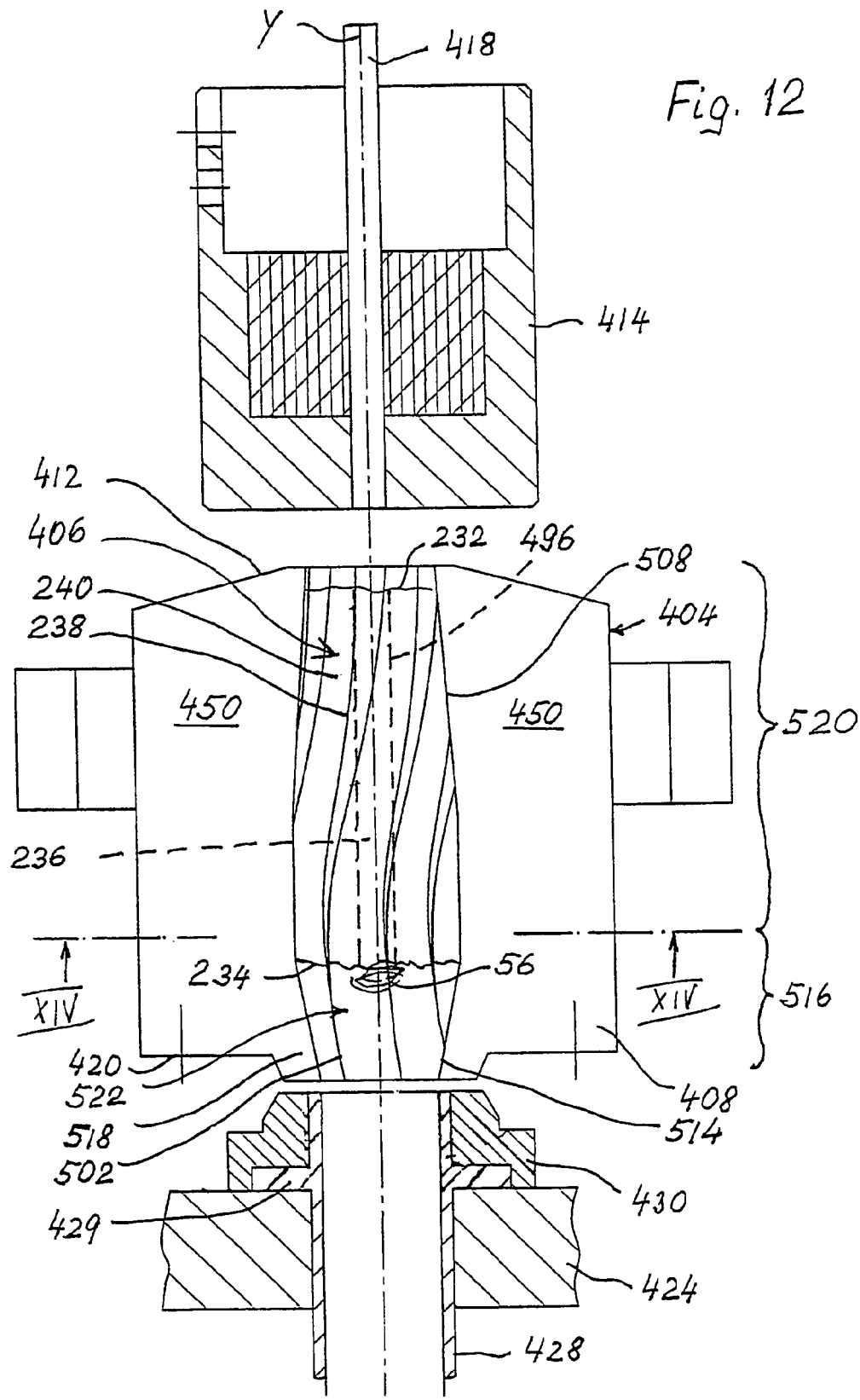
FIG. 12 shows the combined press according to FIG. 11 in its closed or pressing position with a preform.

In a stepwise sequence in time with the press 404, the endless transportation element 424 moves one transportation sleeve 428 at a time into the coaxial position with respect to the outlet side 420 shown in FIG. 11, in order that in each case a preform 406 can be ejected from the press 404 in the final closed or pressing state of the latter into the transportation sleeve 428 by means of the ejecting rod 418 and can be held in a precisely defined rotational position in the transportation sleeve 428, as shown in FIGS. 12 and 24. The transportation element 424 transfers the preform 406 received by the transportation sleeve 428 to the final forming station 410 shown in FIGS. 24 and 25.

The final forming station 410 comprises for the dome-shaped tapering of the introductory end 232 of the preform 406 a dome former 446 which is coaxially movable to and fro and comprises a die 434, which is provided with a coaxial depression 436 tapering in a conical or paraboloidal manner in profile. Pressing ribs 438 project from the wall of this depression 436, radially with respect to its longitudinal axis, and flank pressing grooves 440, which according to FIG. 8 serve for impressing the collecting grooves 242 in continuous extension of the longitudinal grooves 240 and the collecting ribs 244 in continuous extension of the longitudinal ribs 238 at the introductory end 232 of the preform 406 according to FIG. 20. In other words, the preform 406 assumes a precisely defined position in the transportation sleeve 428 after its rotation and axial movement during the ejection from the press 404, in which position the front ends of the longitudinal grooves 240 lie coaxially opposite the pressing ribs 438 and the longitudinal ribs 238 lie coaxially opposite the pressing grooves 440 and they can engage in one another. As a result of this, the tampons 230 leave the press 404 in a state in which the longitudinal grooves 240 go over continuously into the collecting grooves 242 and the longitudinal ribs 238 go over continuously into the collecting ribs 244.

At the same time, the depression 436 of the dome-forming die 434 has the effect of tapering the introductory end 232 in a hemispherical or conical to paraboloidal manner and impressing the finger recess 56, as it is shown in FIG. 10, into the withdrawal end 234 of the preform 406 in the transportation sleeve 428, by means of a recess former 442, in such a way that, after that, the tampon 230 is complete and, if appropriate, can be passed on for further handling, for example to a packing station (not shown).

The rod-shaped recess former 442 has a diameter which is smaller than the inside diameter of the cylindrical transportation sleeve 428, and can be moved coaxially into the transportation sleeve 428 against the withdrawal end 234 of a preform 406 contained therein. A pressing surface on the front face of the recess former 442 has a central, convex, hemispherical projection 444, which is surrounded by an annular surface 445.

The centering cap 430, which lies opposite the die 434 serving for forming the introductory end 232, has a centering cone 447, which fits into an annular clearance 448 in the front face of the die 434 and centers the latter with respect to the transportation sleeve 428.

Figure 13:
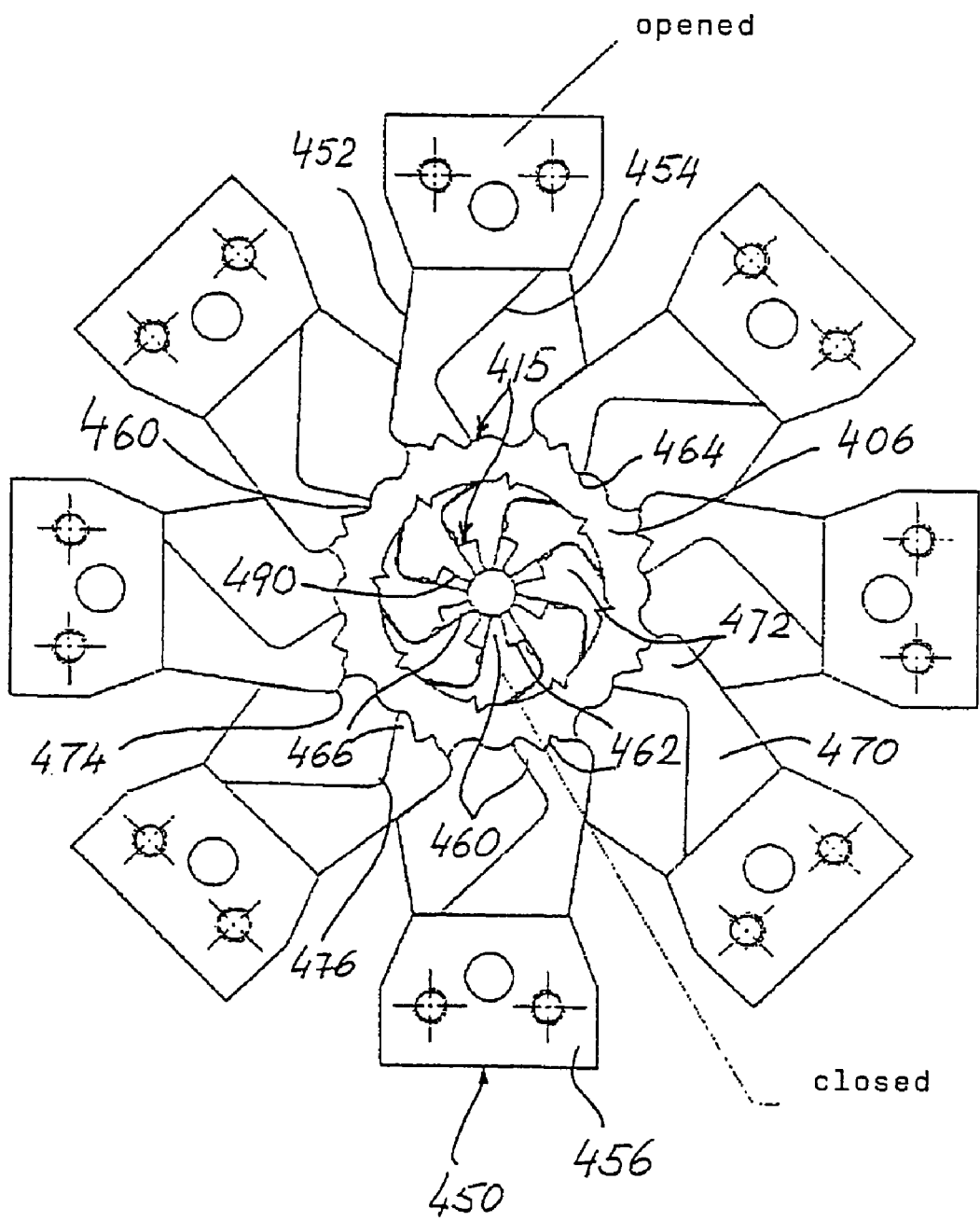
FIG. 13 shows the inlet side of the press in FIGS. 11 and 12, which is shown in the open position with a tampon blank and in the closed position of the pressing jaws with a preform.
Figure 14:
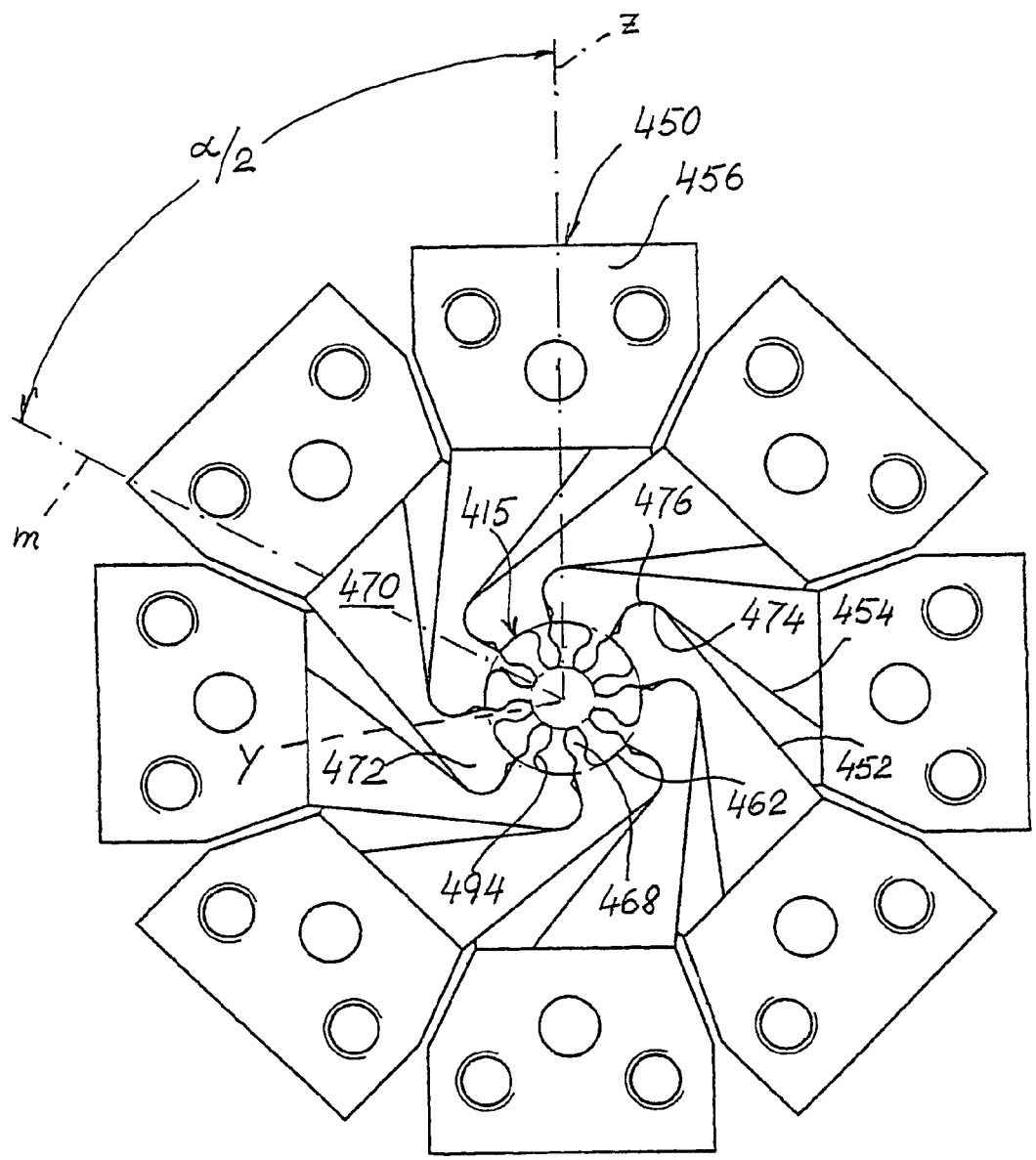
FIG. 14 shows one end of a press-effective longitudinal region of the press according to sectional line XIV-XIV in FIG. 12.
Figure 15:
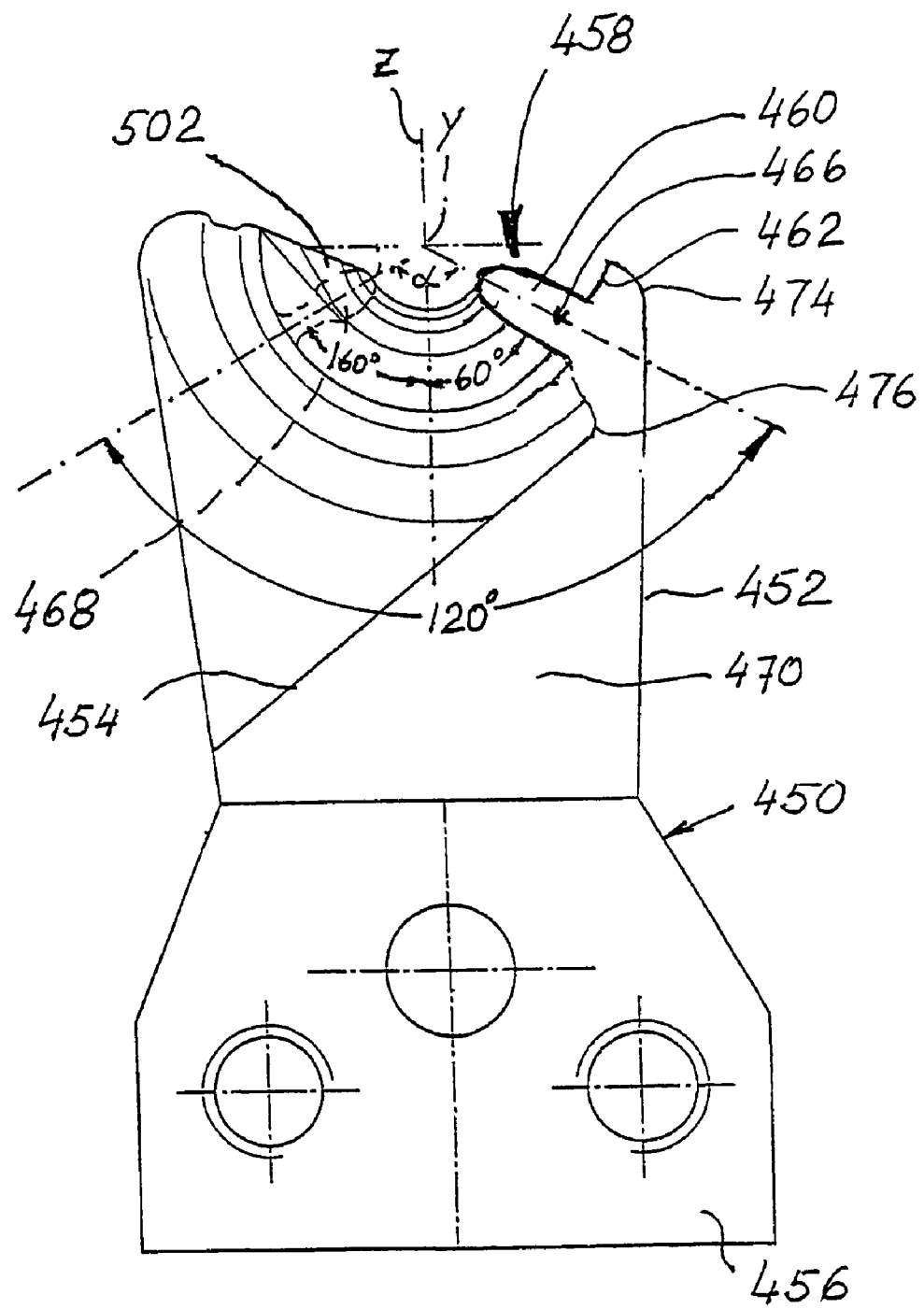
FIG. 15 shows an end view on the inlet side of a pressing jaw on a larger scale.

According to FIGS. 11 to 19, the press 404 comprises eight identical pressing jaws 450 (FIGS. 13 and 14), which are positioned in a star-shaped arrangement relative to a central press axis (y) and which are radially movable synchronously in a common plane relative to the press axis y between their open position and closed position and which support each other at their opposite longitudinal sides 452, 454 in their closed position (FIGS. 13, 14 and 15). Each pressing jaw 450 has a jaw foot 456, which is respectively fastened to a guide bar of the press (not shown). Although it is desired to provide the press 404 with an even number of pressing jaws 450, a different number of pressing jaws, including an odd number of pressing jaws, may be used, on condition that the pressing jaws lie substantially opposite one another in pairs in their pressing or closed position. The number of pressing jaws 450 may vary, for example depending on the weight and the composition of the material used for the tampon, and may be greater or less than eight. However, wherever possible, the number of pressing jaws must not be lower than four.

According to FIG. 15, the pressing jaws 450 respectively have a stepped pressing surface 458, wherein the pressing surfaces 458 of the pressing jaws 450 form the press opening 415 of round cross section (FIG. 13 and 14). Each pressing surface (458) has a pressing knife 460, which is directed toward the press opening 415, and a pressing shoulder 462, which is positioned only at a determined side 490 (FIG. 15) of the pressing knife 460 and is respectively directed in the same circumferential direction around the press axis y.

FIG. 15 shows that the pressing knife 460 has at the inlet side 412 of the press 404 a wedge-shaped transverse profile 466, which has a rounded pressing edge 464 at the inner end, while the pressing shoulder 462 is relatively narrow in comparison in the circumferential direction. In this case, the pressing shoulder 462 is outwardly offset radially with respect to the pressing edge 464 at the free, inner end of the pressing knife 460 relative to the press axis y.

Figure 18:
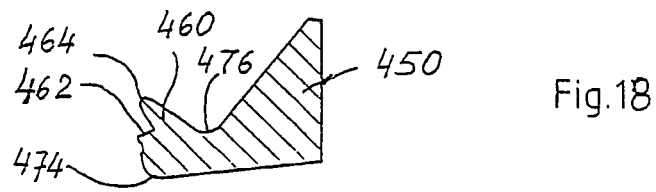
FIG. 18 shows a cross section of the pressing jaw according to line XVIII-XVIII in FIG. 17.

The profile of the pressing jaws 450, which can be seen in the front view of the inlet side 412 of the press 404 in FIGS. 13, 15 and 18, extends substantially on the side of a longitudinal center axis z of each pressing jaw 450 counterclockwise in an L-shaped manner from the jaw foot 456 to the press opening 415. The transverse profile of each pressing jaw 450 is determined in each case by a long L leg 470, which is radially tapered in a triangular form in the direction of a short L leg 472 and, after this tapering, goes over at its radially inner end into a stop head 474. The stop head 474 has a rounded profile and is a component of the thickened, short L leg 472, which is angled away clockwise with respect to the long L leg 470. This angling away has the form of a stop recess 476, the round cross-sectional profile of which extends over an obtuse-angled arc of approximately 90° in the direction of the press opening 415 and corresponds to the cross-sectional profile of the stop head 474 of the clockwise neighboring pressing jaw 450. The end of the short L leg 472 is positioned at a smaller distance from the pressing jaw axis z and forms the pressing edge 464.

In FIG. 14, a longitudinal center axis m of a drop-shaped transverse profile 468 of the pressing knife 460 forms with the longitudinal center axis z of the associated pressing jaw 450 an angle α/2, which respectively opens in the clockwise direction in relation to the longitudinal center axis z of the pressing jaw 450. This angle α/2 between the longitudinal center axis m of the pressing knife 460 and the longitudinal center axis z of the pressing jaw 450 in FIG. 14 corresponds to half the circumferential angle α/2, i.e. 60° in the present case, over which each longitudinal groove 242 extends spirally over the circumferential angle of 120° around the press axis y. It follows from this that the drop-shaped transverse profile 468 of the rear end of the same pressing jaw 450, which end can be seen in FIG. 14, is curved in the clockwise direction with respect to the front pressing jaw profile, shown in FIGS. 13 and 15, or forms an angle with the longitudinal center axis z of the pressing jaw 450 which corresponds to the second half of the circumferential angle α/2 of 60° of the overall circumferential angle of 120°.

FIG. 15 shows more clearly that the pressing shoulder 462 is positioned only at the determined side 490 of the pressing knife 460, which is respectively directed in the same circumferential direction around the press axis y. In this case, the pressing surface 458, respectively comprising the pressing knife 460 and the pressing shoulder 462, of each pressing jaw 450 is spirally formed. Given a diameter of the press opening 415 in the range from 8 to 17 mm, in the closed or pressing position of the press 404, the pressing knife 460 and the associated pressing shoulder 462 of each pressing jaw 450 may extend over a circumferential angle α of up to 190°.

For the pressing jaws 450 of the present exemplary embodiment, which are of a one-part form, a circumferential angle α of the pressing knife 460 and of the pressing shoulder 462 of each pressing jaw 450 of 80° to 190° is provided, in the present case of 120°.

According to FIG. 11, in an intermediate position between their starting position and final end position or closed position, that is before they reach their final end position or closed position, the pressing jaws 450 form with their substantially spiral pressing surface 458 a tangent to an imaginary, barrel-shaped envelope surface 492.

A particularly important feature of the invention consists in that, in their final closed or pressing position according to FIG. 12, the spiral pressing knives 460 of all the pressing jaws 450 form a tangent to an imaginary, substantially circular-cylindrical envelope surface 496 of the fiber column 236. In this final closed or pressing position, the 0° apex point of an arcuate curve 506 (FIG. 11) of all the pressing edges 464 (FIGS. 15, 18 and 19) which enclose the imaginary, circular-cylindrical envelope surface 496 lie on the center longitudinal axis z of each pressing jaw 450 (FIG. 14), wherein the pressing surface 458 extends toward its two axial ends respectively in a complementary manner over half a circumferential angle α/2 in the range of up to 95° of the spiral pressing surface 458 of the pressing jaw 450 (FIGS. 14 and 15).

FIG. 15 reveals more clearly that, at the inlet side 412 of the press 404, the wedge-shaped transverse profile 466 of the pressing knife 460 gradually goes over in the direction of the diameter reduction device 408 (FIG. 12) into the drop-shaped transverse profile 468, the greatest thickening of which lies behind the front, narrow, rounded pressing edge 464, and toward a pressing knife foot 488 there is a neck-like narrowing 494.

Figure 16:
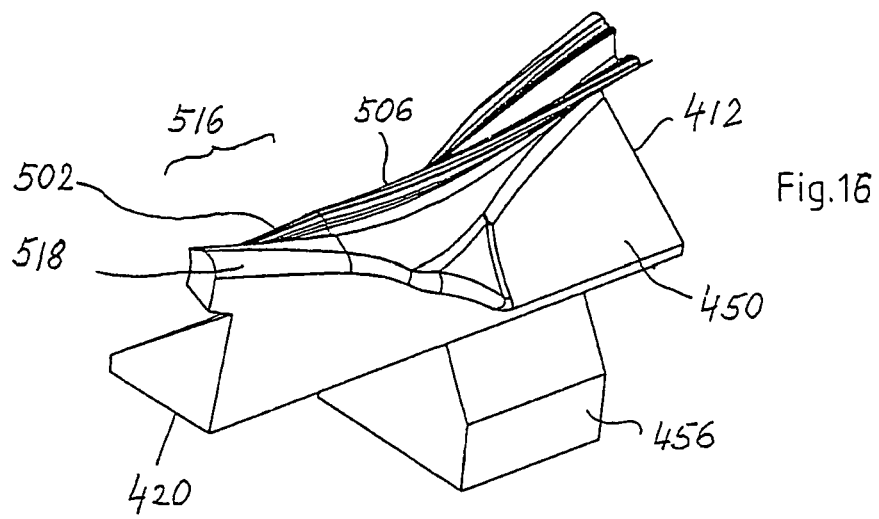
FIG. 16 shows a perspective representation of the pressing jaw in FIG. 15, into which part of the diameter reduction device is integrated.
Figure 17:
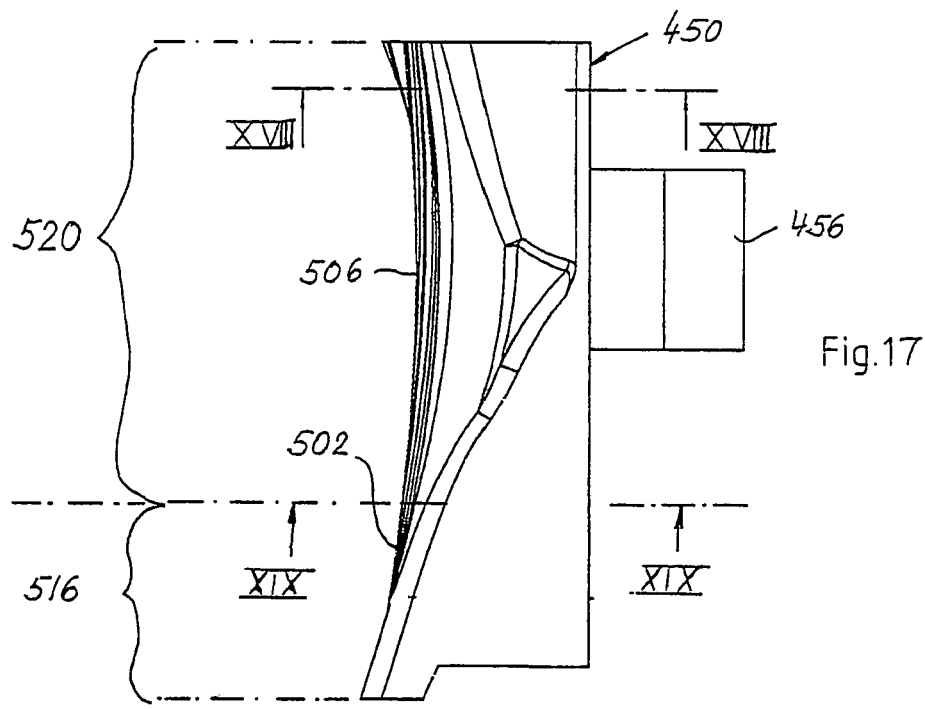
FIG. 17 shows a side view of the pressing jaw in FIG. 16.
Figure 19:
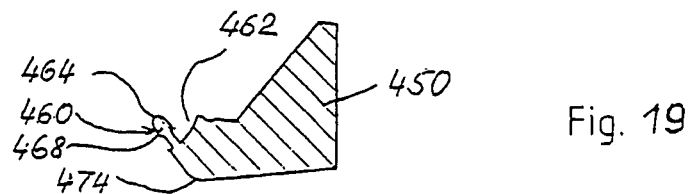
FIG. 19 shows a cross section of the pressing jaw according to line XIX-XIX in FIG. 17.
Figure 21:
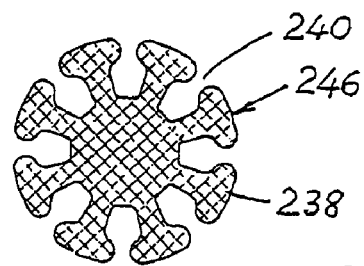
FIG. 21 shows a cross section of the preform according to sectional line XXI-XXI in FIG. 20 in the region of its introductory end.

FIGS. 15, 16 and 17 also show that the end of each pressing shoulder 462 lying in the direction of the outlet side 420 of the press 404 is directed clockwise. As mentioned, the stepped pressing surface 458 of each pressing jaw 450 runs spirally in relation to the press axis y (FIG. 11) and ends with a greatly reduced, inverted V-shaped cross section at the outlet side 420 (FIG. 11) of the diameter reduction device 408 combined with the press 404. At the end of a press-effective region 520 of the press 404 and the beginning of an extension 516 of the press 404, which forms the diameter reduction device 408, the pressing knives 460 go over continuously into forming ribs 502 and the pressing shoulders 462 go over continuously into forming grooves 504 on the inner face of the pressing jaws 450 and in the same spiral form as the stepped pressing surfaces 458. In this case, the inverted V-shaped cross section of the forming ribs 502 on the outlet side 420 of the press 404 is so small that the forming ribs 502 then only perform a guiding function for the longitudinal grooves 240a, which are closed at the circumferential surface 245 of the security zone 254 of the tampon 230, during the ejection of the tampon 230 from the press 404 and the diameter reduction device 408 (FIGS. 11 and 12). In this case, the pressing knife 460 and the associated pressing shoulder 462 of each pressing jaw 450 extend over the circumferential angle α of 120° of the tampon 230 between the two ends of the same, that is to say between the inlet side 412 and the end of the press-effective region 520 of the press 404. Half the circumferential angle α/2 respectively extends in the present case over 60° of the press-effective region 520 of the press 404 in a symmetrical or complementary manner on both sides of the center longitudinal axis z of each pressing jaw 450, with the result that the pressing jaw 450 is loaded uniformly over its entire cross section by the pressing forces exerted.

The pressing knives 460 and pressing shoulders 462 of each pressing jaw 450 are not only spirally curved in the longitudinal direction in a way corresponding to the described circumferential angle α of the tampon 30 of 120°, but also have the spiral curvature 506 from one end of the pressing jaw 450 to the other end of the same pressing jaw 450 (FIGS. 11, 16 and 17). This curvature 506 is obtained because the effective pressing surface 458 of each pressing jaw 450 must press the spiral longitudinal grooves 242, which must respectively extend over a specific circumferential angle α of the preform 406 in FIG. 20, i.e. in present case over 120° of the circumferential surface of the approximately cylindrical preform 406 in the specific angle of lead β (FIG. 8). In this case, the preform 406 (FIG. 20) is compressed altogether to the degree of pressing of the tampon 230 (FIGS. 12, 13 and 14), in the case of which each pressing knife 460 moves into a position directed toward the press axis y and the inner pressing edges 464 of the pressing knives 460 form a tangent to the imaginary, cylindrical envelope surface 496 of the fiber column 236 (FIG. 12). As a result of this, the clear cross section of the press opening 415 formed by the pressing jaws 450 is widened in a barrel-shaped manner from its two ends up to the longitudinal center of the pressing jaws 450, before the pressing jaws 450 reach their final pressing position, in which the pressing edges 464 assume the circular-cylindrical pressing dimensions.

On the other hand, according to a very important feature of the invention, in their pressing or closed position, the pressing shoulders 462 surround an imaginary, slightly circular-frustoconical envelope surface, to which the outer ends of the longitudinal ribs 240 of the preform 406 form a tangent at the circumferential surface 245 of the same and the diameter of which is widened in the direction of the outlet side 420 of the press 404, as the pressing position of the press 404 in FIG. 12 and of the preform 404 in FIG. 20 clearly illustrate. This conicity, widened in the direction of the outlet side 420, of the pressing shoulders 462 of all the pressing jaws 450 has the great advantage that, without releasing the press 404, i.e. synchronously moving the pressing jaws 450 out of their final closed position by a certain amount radially outward in the opening sense, the preform 406 shown in FIGS. 12 and 20 can be ejected from the press 404, by turning about its longitudinal axis x, which is coaxial to the press axis y, and without damaging the fiber structure on its outer surface by the diameter reduction device 408 and the centering cap 430, into a transportation sleeve 428 and, if appropriate, passed on for further handling. This saves a working step and control effort required for it, whereby the saving makes an increase in the production output possible. At the same time, the diameter reduction device 408, which is tapered conically toward the outlet side 420, ensures that the longitudinal grooves 240 are closed in the region of the security zone 254 and, in the direction of the introductory end 232 gradually open and widen up to the collecting grooves 242, on account of the conical tapering of the preform 406.

This final degree of closing corresponds to a tangent B in FIG. 11, which is applied to an apex point 0° of the radially outwardly bent curvature 506 of a pressing knife 460 and is likewise directed parallel to the press axis y. The pressing edges 464 of the pressing knives 460 consequently form the circular-cylindrical envelope surface 496 of the fiber column 236 for the ejection of the preform 406 in FIGS. 12 and 20. As a result of this, the preform 406 is guided satisfactorily and precisely during ejection, while at the same time performing an axial and rotational movement, by the pressing knives 460 of the pressing jaws 450 engaging in the longitudinal grooves 240 of the preform 406. On the other hand, the imaginary envelope surface 508, which is widened conically toward the outlet side 420, of the pressing shoulders 462 of all the pressing jaws 450 has the effect, after a short ejecting movement of the preform 406, that the radially outer ends of the longitudinal ribs 238 of the preform 406, which form the circumferential surface 245 of the preform 406, are released by the pressing shoulders virtually immediately and, as a result, a significant frictional resistance between the pressing shoulders 462 of the pressing jaws 450 and the longitudinal ribs 238 of the preform 406 is eliminated.

The outward displacement of the fiber material achieved by the form of the pressing jaws 450 makes it possible to save fiber material, now requiring in the case of the exemplary embodiment described, of a digital tampon 230 with a final diameter of 13 mm and a length of 50 mm, only 2.4 g of fiber material to be used, as compared with previously 2.7 g of fiber material. 75% of the fiber material is made up here of highly expansive fibers of irregular, for example star-shaped, cross section, and 25% is made up of cotton fibers.

As a departure from the embodiment represented, the press may also be divided transversely with respect to its longitudinal axis, as is described in PCT/EP 02/03262, with the result that the divided pressing jaws are movable to and fro independently of each other radially with respect to the press axis y. The pressing jaws 450 may be divided in at least one plane which is directed normal to the press axis y. In the case of a two-part configuration of the pressing jaws 450, it is preferred for the parting plane of the two-part pressing jaws, the 0° apex point of their pressing surface and the axis y of the press 404 to intersect at the longitudinal center point of the press-effective longitudinal portion. By multiple division of the pressing jaws 450 transversely with respect to the press axis y and according to the number of pressing jaws 450, the circumferential angle α can be extended beyond 150°. Furthermore, it is possible by suitable shaping of the pressing jaws 450 to change the outer contour of the preform according to the specific requirements which the preform has to meet.

To sum up from the foregoing description of the pressing jaws 450 according to the invention, it can be stated that, in their closed position, the pressing jaws 450 must lie substantially diametrically opposite one another.

Figure 23:
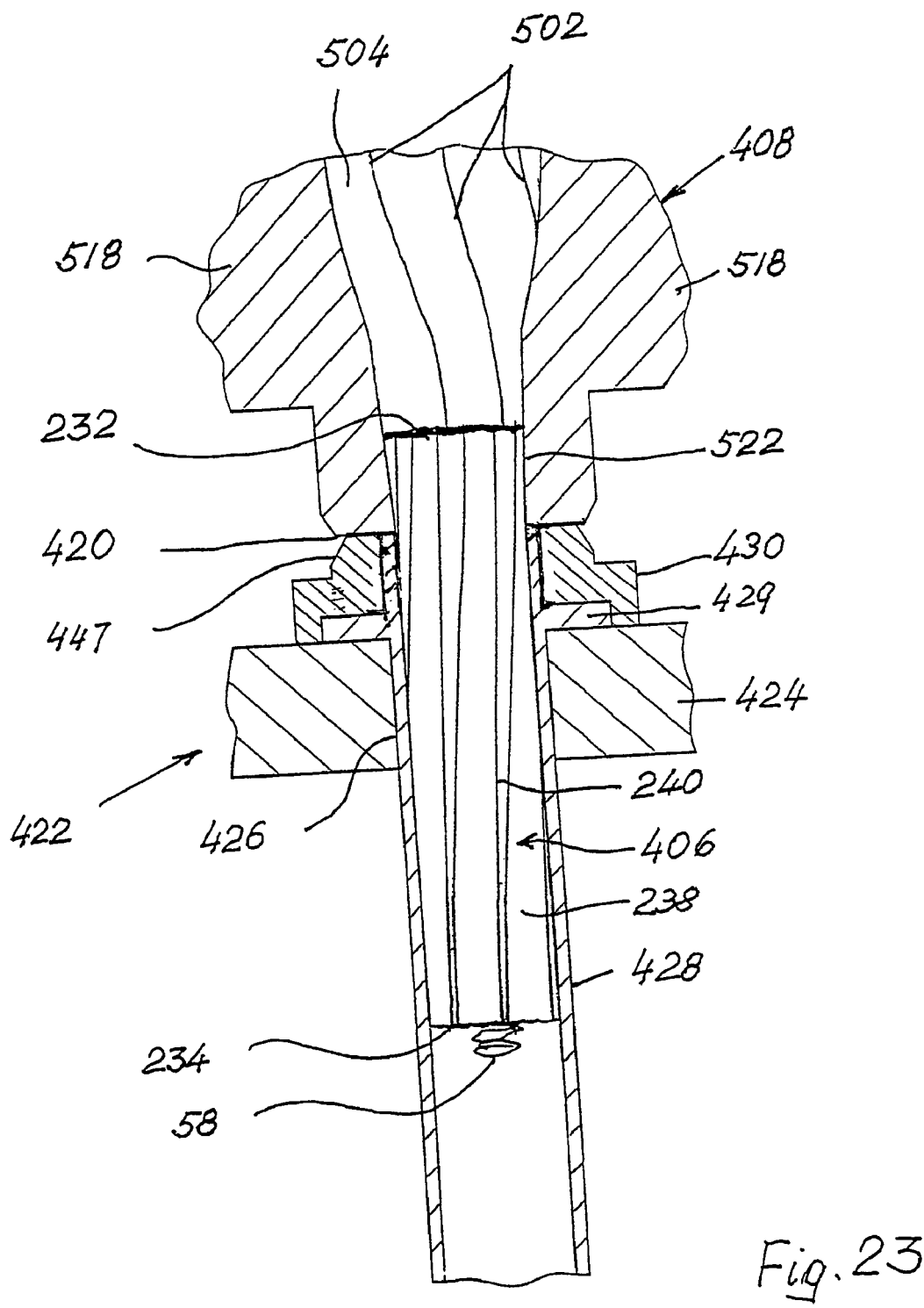
FIG. 23 shows the outlet side of the combined press with the diameter reduction device and of a transportation device positioned in front of the outlet side and the preform transferred partially into a transportation sleeve, in a central longitudinal section.

Shown in FIGS. 11, 12 and 23 is the diameter reduction device 408, which is integrated into the press 404 and comprises the extension 516 of the pressing jaws 450 in the direction of the outlet side 420 of the press 404. Forming jaws 518 on the outlet side of the pressing jaws 450 are arranged directly behind the press-effective longitudinal portion or region 520 of the pressing jaws 450 in which the pressing jaws 450 are provided, as described, with the pressing knives 460 and pressing shoulders 462 for pressing the preform 406. These forming jaws 518 on the outlet side, which extend the pressing jaws 450, form in the closed state of the press 404 a forming cone 514, which forms a conical forming channel 522 for the preforms 406.

FIGS. 12 and 23 show that the pressing knives 460 go over continuously into the spiral forming ribs 502 and engage directly in the spiral longitudinal grooves 242 of a preform 406 leaving the combined press 404 (FIG. 20), in order to press said preform slightly in a concentric manner and smooth it, so that the profile of the preform 406 is retained, but a widening 37 of the cross section of the fiber column 238 (FIG. 10) is reduced.

According to FIGS. 11, 12 and 23, the spiral forming ribs 502, the cross section of which decreases to an ever greater extent, end at the outlet side 420 of the forming cone 514, which is formed by the closed pressing jaws 450, tapered toward the outlet side 420 and behind which the smooth-walled, cylindrical entry stub 428a of the transportation sleeve 428 is arranged. The end of the forming cone 514 has a clear diameter which largely corresponds to the clear diameter of the entry stub 428a of the transportation sleeve 428. In this forming cone 514, the spiral longitudinal ribs 238 of the preform 406, which up to this point are slightly T-shaped in cross section, are pressed radially with respect to the press axis y and smoothed, so that the bars 246 of the T-shaped longitudinal ribs 238 (FIGS. 21) are widened in the circumferential direction of the preform 406 and, as a result, the longitudinal grooves 240 which are drop-shaped in transverse profile (FIG. 22) in the region of the withdrawal end 234 of each preform 406 are closed, in order to form the security zone 254, which is closed at the circumferential surface of the preform 406 (FIG. 8), with the collecting channels 248 contained and ending therein.

Since, during the ejection from the press 404, which is kept in the closed state, and from the diameter reduction device 408 integrated in it, into the transportation sleeve 428, the preform 406 is simultaneously subjected in one operation to a rotation by the longitudinal ribs 238, longitudinal grooves 240; forming ribs 502 and forming grooves 504, it is ensured by the cylindrical inlet stub 428a of the transportation sleeve 428, which is conically widened over a small length at its inlet opening, that the high quality of the outer surface and of the fiber structure of the preform 406 is retained.

As known from U.S. Pat. No. 5,832,576, the process for manufacturing the tampon 230 described above comprises the provision of a random-fiber nonwoven in strip form, the width of which preferably corresponds approximately to the length of the tampon 230, by cutting off a section of length from the random-fiber nonwoven, which has a withdrawal cord 58 wrapped around it (FIG. 10), and subsequently winding the section of length upon itself to form a substantially cylindrical tampon blank or a wound blank. On the outer side of the nonwoven strip that lies on the outside while the tampon blank is being produced, a fluid-permeable layer is at least partially applied before the winding-up operation, said layer being fastened at least partially on the outer side of the section of nonwoven strip, preferably by heat-sealing. At least one nonwoven layer or else a thermoplastic, heat-sealing, perforated film of plastic may be used, in order to cover the circumferential surface of the tampon 230 at least partially, the cover material preferably being hydrophobic (FIG. 8).

Subsequently, the preferably cylindrical tampon blank, the withdrawal end 234 of which lies at the front in the feeding direction or in the direction of the press 404, is coaxially introduced into the press 404 by means of the feeding ram 414. After that, the tampon blank is radially compressed by the pressing jaws 450 in the front, inlet-side, press-effective region 520 of the press 404, in each case on identical, narrow, spiral-shaped portions of identical angle of lead β of its circumferential surface, separated from one another by the same circumferential angles. In this case, the spiral-shaped portions are respectively pressed over a circumferential angle α of up to 190°, preferably over an angle of 80° to 120°, in the present case of an angle of 120°. During the pressing, the tampon blank is initially given a barrel-shaped contour with spirally running longitudinal grooves 240 which are slightly undercut and then increasingly drop-shaped in transverse profile in the direction of the withdrawal end and surround the fiber column 236, which is substantially cylindrical but, because of the barrel form, is widened in cross section over the middle of its length and pressed more intensely at the ends. From the fiber column 236 there extend radially outward and in the longitudinal direction of the preform 406 spirally running longitudinal ribs 238 of smaller cross section, which in transverse profile are initially slightly T-shaped and increasingly drop-shaped.

As a result of the press opening 415, formed by the pressing shoulders 462, which conically widens slightly in cross section up to the end of the press-effective region 520 of the press 404 in FIG. 12, the free, outer ends of the longitudinal ribs 238 are subjected in the press 404 to an increasingly smaller radial pressing pressure from the withdrawal end 234 of the preform 406, lying at the front in the press 404, to its introductory end 232, lying at the rear in the press 404, with the result that the longitudinal grooves 240 are increasingly wider or open at the circumferential surface 245 in the direction of the introductory end 232 lying at the rear in the press 404. Depending on the specific intended purpose of the tampon to be pressed, a widened cross section of the fiber column 236 may also be considered. Such a widening, which could extend for example over the length of the security zone 254, may, depending on the form of the pressing edges 464, be a cylindrical widening or a conical widening toward the withdrawal end 234. It is preferred, however, to widen the fiber column 236 conically over its entire length toward the withdrawal end 234.

Depending on the properties of the fiber material used, in particular when using highly expansive fibers of irregular cross section with a high recovery (memory effect), the preform 406 may be pressed to its final form at a temperature of the pressing jaws 450 of 80° to 120° C., in order to achieve the desired dimensional stability of the fiber material by eliminating the memory effect of the fibers, which on contact with body fluid immediately becomes active again, and consequently increases the rate of expansion and absorption of the tampon 230 with reduced use of fiber material.

Therefore, in the final closed state of the press 404, a tampon blank is compressed in a single pressing operation to form the preform 406, in the case of which the width of the longitudinal grooves 240 is reduced as a result of the pressing knives 460 changing from the inlet side 412 to the outlet side 420 of the press 404 from a wedge-shaped transverse profile 466 into a drop-shaped transverse profile 468 (FIG. 15), with simultaneous widening of the T-bars 246 of the T-shaped longitudinal ribs 238, as the cross sections in FIGS. 6 and 7 show.

During the ejection from the press 404, the preform 406 is at the same time subjected to a final shaping in the forming cone 514 formed by the closed pressing jaws 450. This final shaping consists in that a slight radial pressure is exerted on the outer ends of the spiral longitudinal ribs 238 and on the spiral longitudinal grooves 240 by the forming cone 514, which can be heated if desired to 80° C. to 120° C., and the forming channel 522 of the latter with its forming ribs 502 and forming grooves 504. This slight radial pressure, exerted in the forming channel 522, has the effect that the outer ends of the bars, directed in both circumferential directions of the preform 406, of neighboring longitudinal ribs 238, which are T-shaped in transverse profile, are respectively pressed initially against each other and closed by the radial compression and the accompanying reduction in the diameter in the region of the withdrawal end 234, but remain increasingly open in the direction of the introductory end 232 of the conical preform 406 on account of its decreasing diameter. As a result, the outwardly closed, soft, approximately cylindrical circumferential surface 245 of the security zone 254 of the preform 406 is formed, the fiber material of which surrounds and axially closes the spiral collecting channels 248.

When, as a concomitant effect of the rotational movement, the finished pressed preform 406 leaves the forming cone 514, formed by the pressing jaws 450, into the transportation sleeve. 428 of the transportation device 422, the freshly compressed fiber material expands with respect to the very smooth, wide cylindrical inside wall of the transportation sleeve 428, without any frictional resistance that impairs the surface quality occurring between the inside wall of the transportation sleeve 428 and the fiber material at the outer surface of the preform 406, with the result that the high quality of the tampon 230 provided with spiral longitudinal ribs 238 and longitudinal grooves 240 is also ensured in the case of mass production.

Subsequently, the preform 406 ejected into the transportation sleeve 428 is transported by means of the transportation device 422 in front of the pressing station 410 (FIG. 24). After that, the dome former 446 is moved with its centering depression 436 coaxially against the centering cone 447 and centered. In this working position, the dome former 442 is moved into the transportation sleeve 428 and against the withdrawal end 234 of the preform 406, in order to press the preform 406, lying in the precisely defined rotational position, with its introductory end 232 against the pressing ribs 438 and pressing grooves 440 in the depression 436 of the die 434. In this way, the finger recess 56 is impressed into the withdrawal end 234 of the preform 406 by means of the projection 444 of the recess former 423 and, at the same time, the trough-shaped collecting grooves 440 and the cross-sectionally inverted V-shaped collecting ribs 244 are impressed into the introductory end 232 of the preform 406 by means of the pressing ribs 438 and the pressing grooves 440 in the depression 436 of the die 434. This axial pressing of the preform 406 is accompanied by the desired densification of the fiber material of the collecting ribs 438 and collecting grooves 440 at the introductory end 232 and of the finger recess 56 at the withdrawal end 234, which forms the rear end of the security zone 254, surrounding and closing the collecting channels 248, of the then completed tampon 230 according to FIG. 8.

The invention claimed is:

1. Tampon for feminine hygiene, with a tapered introductory end, a withdrawal end provided with a withdrawal means and a longitudinal axis, comprising a longitudinally extending absorbent body made from compressed fiber material, the absorbent body being densified more intensely in the region of the longitudinal axis and forming a fiber column, from which longitudinal ribs extend radially outward and flank longitudinal ribs in pairs, wherein the tapered introductory end is provided with collecting grooves and collecting ribs to collect menstrual secretions, wherein the collecting grooves are open axially to the front and radially outward and wherein the collecting ribs flank the collecting grooves.

2. Tampon of claim 1, wherein the collecting grooves transition continuously into the longitudinal grooves and the collecting ribs transition continuously into the longitudinal ribs at the end of the tapered introductory end.

3. Tampon of claim 1, wherein a front end of the collecting grooves in the fiber column has an approximately V-shaped cross section.

4. Tampon of claim 1, wherein collecting grooves have a substantially trough-shaped cross section and the collecting ribs have a narrow cross section being tapered outward.

5. Tampon of claim 1, wherein a middle longitudinal portion of the collecting grooves has a greater width than the longitudinal grooves and that the collecting ribs are more intensely densified than the longitudinal ribs.

6. Tampon of claim 1, wherein the inner width of the collecting grooves is about 1.0 to 2.5 mm.

7. Tampon of claim 1, wherein the cross section of the longitudinal grooves is slightly undercut and that they form, in transverse profile, collecting pockets, and that the longitudinal ribs have a slightly T-shaped transverse profile.

8. Tampon of claim 1, wherein the longitudinal grooves have a slightly undercut transverse profile of a collecting pocket from the rear end of the tapered introductory end, wherein said undercut transverse profile is increasingly drop-shaped toward the withdrawal end, wherein the longitudinal grooves are increasingly narrower at the circumferential surface of the tampon and are closed in the region of a security zone at the withdrawal end to form axially parallel collecting channels, which are closed by the fiber material of the security zone in front of the withdrawal end.

9. Tampon of claim 8, wherein the drop-shaped transverse profile of the longitudinal grooves are radially expanded toward the fiber column.

10. Tampon of claim 1, wherein the fiber column is pressed approximately cylindrically along its entire length.

11. Tampon of claim 1, wherein the longitudinal grooves, longitudinal ribs and collecting channels extend approximately parallel to the tampon axis.

12. Tampon of claim 1, wherein the longitudinal grooves, longitudinal ribs and collecting channels extend spirally or helically around the longitudinal axis of the tampon.

13. Tampon of claim 1, wherein the longitudinal grooves, longitudinal ribs and collecting channels extend over an circumferential angle of up to 190°.

14. Tampon of claim 1, further comprising a security zone at the withdrawal end in which the longitudinal grooves are closed by the fiber material in front of the withdrawal end, wherein some of the longitudinal grooves end at the security zone.

15. Tampon of claim 1, further comprising a security zone at the withdrawal end in which the longitudinal grooves are closed by the fiber material in front of the withdrawal end, wherein the longitudinal ribs are radially pressed less intensive radially in the region of the security zone.

16. Tampon of claim 1, wherein the fiber material of the longitudinal ribs is pressed increasingly less intensive radially from the introductory end up to the region of the withdrawal end and therefore is smoother at the circumferential surface of the tampon than at the introductory end.

17. Tampon of claim 1, further comprising a security zone at the withdrawal end in which the longitudinal grooves are closed by the fiber material in front of the withdrawal end, wherein the fiber material of the security zone is hydrophobically impregnated.

18. Tampon of claim 1, further comprising a security zone having an axial length of 5 to 15 mm at the withdrawal end in which the longitudinal grooves are closed by the fiber material in front of the withdrawal end.

19. Tampon of claim 1, wherein a finger recess is axially pressed into the withdrawal end of the tampon, wherein the intensely densified fiber material of the finger recess closes the end of the collecting channels extending up to the withdrawal end.

20. Tampon of claim 19, wherein the axial length of the more intensely densified fiber material of the finger recess is up to approximately 5 mm.

21. Tampon of claim 1, wherein the outer surface of the tampon is at least partially covered by fluid-permeable cover.

22. Tampon of claim 21, wherein the cover consists of a non-woven layer.

23. Tampon of claim 21, wherein the cover consists of a perforated foil.

24. Tampon of claim 21, wherein the cover is a hydrophobic cover.

25. Tampon of claim 1, wherein the circumferential surface of the tampon is substantially cylindrical.

* * * * *